(12) United States Patent
Rhee et al.

(10) Patent No.: US 8,227,445 B2
(45) Date of Patent: Jul. 24, 2012

(54) METHODS OF TREATING HYPERTENSION

(75) Inventors: Sung W. Rhee, Little Rock, AR (US);
Paul L. Hermonat, Little Rock, AR (US); Nancy J. Rusch, Bigelow, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 13/051,508

(22) Filed: Mar. 18, 2011

(65) Prior Publication Data

US 2011/0213018 A1 Sep. 1, 2011

Related U.S. Application Data

(62) Division of application No. 12/109,756, filed on Apr. 25, 2008, now abandoned.

(60) Provisional application No. 60/914,718, filed on Apr. 27, 2007.

(51) Int. Cl.
*A01K 43/04* (2006.01)
*A61K 31/715* (2006.01)
*A61K 48/00* (2006.01)
*A01N 63/00* (2006.01)

(52) U.S. Cl. ............... 514/44; 424/93.2; 424/93.21

(58) Field of Classification Search ............ 514/44; 424/93.2, 93.21
See application file for complete search history.

(56) References Cited

U.S. PATENT DOCUMENTS

| | | | | |
|---|---|---|---|---|
| 5,837,534 A | * | 11/1998 | Olson et al. | 435/320.1 |
| 6,239,117 B1 | * | 5/2001 | Christ et al. | 514/44 R |
| 6,297,221 B1 | * | 10/2001 | Parmacek et al. | 514/44 R |
| 7,030,096 B1 | * | 4/2006 | Geliebter et al. | 514/44 R |

FOREIGN PATENT DOCUMENTS

| | | | |
|---|---|---|---|
| CA | 2405652 | * | 3/2004 |
| JP | 2005/154428 | * | 6/2005 |
| JP | 2005154428 2 B | | 6/2005 |

OTHER PUBLICATIONS

Yamamura (J. Biochem, 1997, vol. 122, p. 157-167.*
Pallanck (Human Mol. Genet., 1994, vol. 3, No. 8, p. 1239-1243.*
Yamauchi-Takihara (PNAS, 1989, vol. 86, No. 10, p. 3504-3508).*
Epp (Genomics, 1993, vol. 18, No. 3, p. 505-509).*
Yamamura et al. structure and Expression of the Human SM22a Gene, Assignment of the Gene to Chromosome 11, and Repression of the Promoter Activity by Cytosine DNA Methylation, J. Biochem, 1997, pp. 157-167, vol. 122.
Israili et al, The Future of Antihypertensive Treatment, Am J. of Therapeutics, 2007, pp. 121-134, vol. 14.
Melman et al, hMaxi-K Gene Transfer in Males with Erectile Dysfunction: Results of the First Human Trial, Human Gene Therapy, 2006, pp. 1165-1176, vol. 18.
Melman et al, Plasmid-based Gene Transfer for Treatment of Erectile Dysfunction and Overactive Bladder: Results of a Phase I Trial, IMAJ, 2007, pp. 143-146, vol. 9.
Wang et al, AAV delivery of mineralocorticoid receptor shRNA prevents progression of cold-induced hypertension and attenuates renal damage, Gene Therapy, 2006, pp. 1097-1103, vol. 13.
Office Action dated Sep. 20, 2010 from related U.S. Appl. No. 12/109,756, 13 pages.
Pallanck et al, Cloning and characterization of human and mouse homologs of the *Drosophila* calcium-activated potassium channel gene, slowpoke, Human Molecular Genetics, 1994, pp. 1239-1243, vol. 3, No. 8.

* cited by examiner

*Primary Examiner* — Michael C. Wilson
(74) *Attorney, Agent, or Firm* — Polsinelli Shughart PC

(57) ABSTRACT

The invention encompasses a composition for regulating smooth muscle cells. In particular, the invention encompasses a vector comprising a smooth muscle promoter operably-linked to a nucleic acid encoding a calcium-activated potassium channel.

4 Claims, 10 Drawing Sheets
(3 of 10 Drawing Sheet(s) Filed in Color)

A

B

C

METHODS OF TREATING HYPERTENSION

CROSS REFERENCE TO RELATED APPLICATIONS

This application is a divisional of U.S. application Ser. No. 12/109,756, filed Apr. 25, 2008, which claims the priority of U.S. provisional application No. 60/914,718, filed Apr. 27, 2007, each of which is hereby incorporated by reference in its entirety.

GOVERNMENTAL RIGHTS

This invention was made with government support under RO1 HL59238-08 awarded by the National Institutes of Health. The United States government has certain rights in this invention.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

FIELD OF THE INVENTION

The invention encompasses a composition for regulating smooth muscle cells.

BACKGROUND OF THE INVENTION

Nearly 60 million Americans are estimated to suffer from systemic hypertension, and the hallmark finding of this disease is an abnormally high peripheral vascular resistance. Additionally, vasospasm is a finding in some forms of coronary, cerebral and systemic arterial occlusions and also can occur during or after angioplasty to relieve vascular stenoses. New therapeutic approaches are needed to reduce the anomalous vascular tone. For example, only about one-third of patients with essential hypertension (i.e., hypertension of unknown etiology) are successfully treated by standard antihypertensive drugs, and most of these patients require daily, multi-drug therapy to achieve blood pressure reduction, which may lead to one or more side effects.

High-conductance voltage- and calcium-activated potassium channels, named "BK channels" because of their big unitary conductances (150 to 300 pS), are expressed in all vascular beds. The opening of these channels mediates a hyperpolarizing potassium current that buffers contraction of vascular smooth muscle cells (VSMCs) in the arterial wall, resulting in vasodilation of small arteries and arterioles. The $\alpha$ subunit of the BK channel forms the ion-conducting pore, and appears to arise from a single gene family, although phenotypic diversity may be generated by a high level of alternative splicing of the common primary transcript. The BK channel complex also includes a $\beta$ subunit that increases the sensitivity of the $\alpha$ subunit to intracellular calcium, thereby enhancing its activation level. Deletion of the subunit in KO mice to create poorly functional BK channels results in a blood pressure elevation of approximately 20 mm Hg.

During vascular activation caused by vasoconstrictor stimuli, membrane depolarization and the associated rise in cytosolic calcium act synergistically to further open BK channels. Thus, the BK channels buffer VSMC excitation and prevent abnormal arterial contraction by exerting a vasodilator influence. However, this vasodilator influence cannot fully dampen anomalous vasoconstriction under some conditions, including local vasospasm and during pulmonary or systemic hypertension in which an elevated arterial tone persists despite the activation of compensatory mechanisms. Under these conditions, therapeutic interventions are required to restore normal levels of vascular tone.

A unique vasodilator therapy comprising the long-term expression of a potent endogenous vasodilator protein in smooth muscle cells has clear advantages over standard antihypertensive drugs in terms of cost, convenience, and tissue and target specificity. Such a method may provide long-term vasodilation with few side effects compared to standard vasodilator and antihypertensive therapies.

The long-term delivery of BK channels to VSMCs using a smooth muscle-specific promoter provides at least two important advantages. First, its hyperpolarizing influence may limit further increases in vascular resistance and blood pressure during the pathogenesis of hypertension. Second, a higher density of BK channels may prevent or alleviate anomalous vasoconstriction and vasospasm in a single vessel or in a vessel network.

SUMMARY OF THE INVENTION

Hence, one aspect of the present invention encompasses a vector. The vector comprises a smooth muscle specific promoter operably linked to a nucleic acid sequence encoding a calcium-activated potassium channel.

Another aspect of the invention encompasses a method for regulating the blood pressure of a mouse. The method comprises administering to the mouse a vector comprising a smooth muscle specific promoter operably linked to a nucleic acid sequence encoding a calcium-activated potassium channel.

Yet another aspect of the invention encompasses a method of expressing a calcium-activated potassium channel in a smooth muscle cell. The method comprises contacting the smooth muscle cell with a vector comprising a smooth muscle specific promoter operably-linked to a nucleic acid sequence encoding a calcium-activated potassium channel.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

SM22-BKα ($10^{11}$ vp/kg). After 3 weeks, Ang II was infused to induce hypertension, and then SBP was measured for two weeks to evaluate the antihypertensive effect of the therapeutic vectors on the established phase of hypertension. Compared to GFP, AAV-mediated delivery of AAV/MusB-BKα or AAV/SM22BKα significantly lowered blood pressure, and the effect appeared to be dose-dependent. Mean+SD (n=4, 5). * and #: different from Control and GFP, respectively. (P<0.05)

Figure 4:
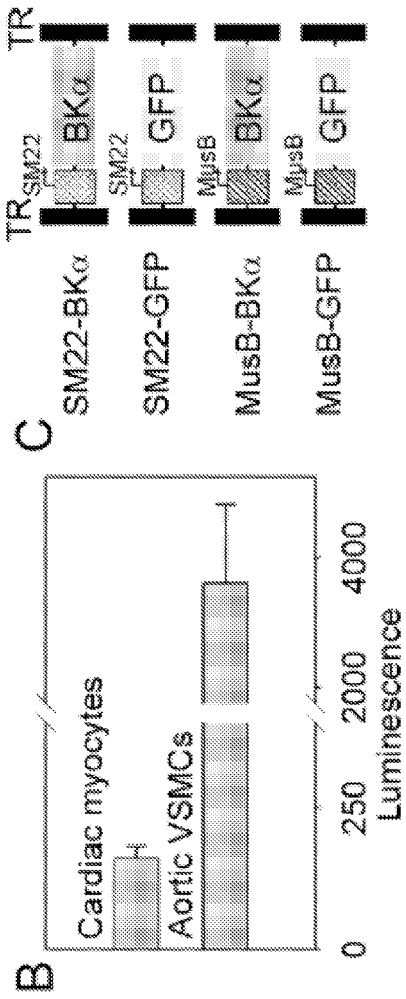

FIG. 4 depicts illustrations of vectors and promoters of the invention, and a graph showing promoter activity. A) DNA sequence of the SM22α and MusB promoters. Bolded sequences represent CArG boxes (SM22α) or a modified CArG sequence (MusB). B) Luciferase assay showed ~20-fold higher activity of MusB in rat aortic VSMCs compared to rat cardiac myocytes. C) The four AAV constructs. The SM22α or MusB promoters will be used to drive expression of GFP (control) or the nucleic acid of interest, BKα.

Figure 5:
Figure 5:
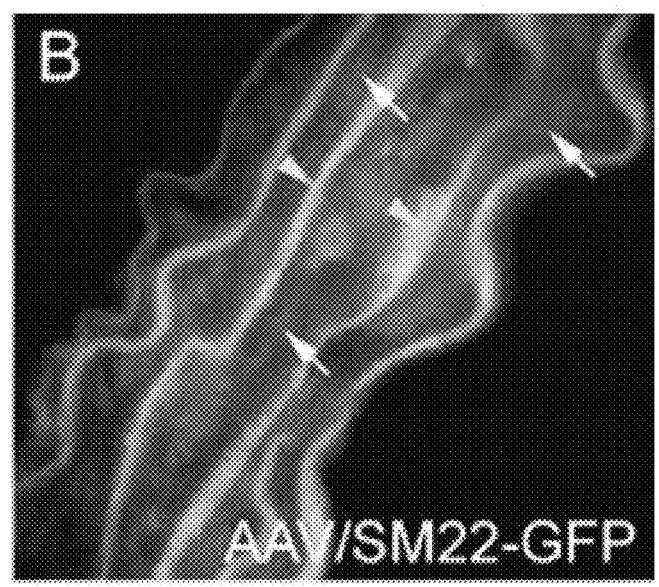

FIG. 5 depicts photographs of the expressed constructs. A) Green fluorescence from A7r5 cells 72 hr after transfection with SM22-GFP or MusB-GFP plasmids. B) Mouse aorta collected 9 wks after injecting AAV/SM22-GFP. VSMCs show green fluorescence (arrows) when stained with Alexa488-labeled anti-GFP antibody. Autofluorescence from connective layers is seen as yellow (yellow arrowheads) and nuclei were stained with DAPI (blue).

Figure 6:
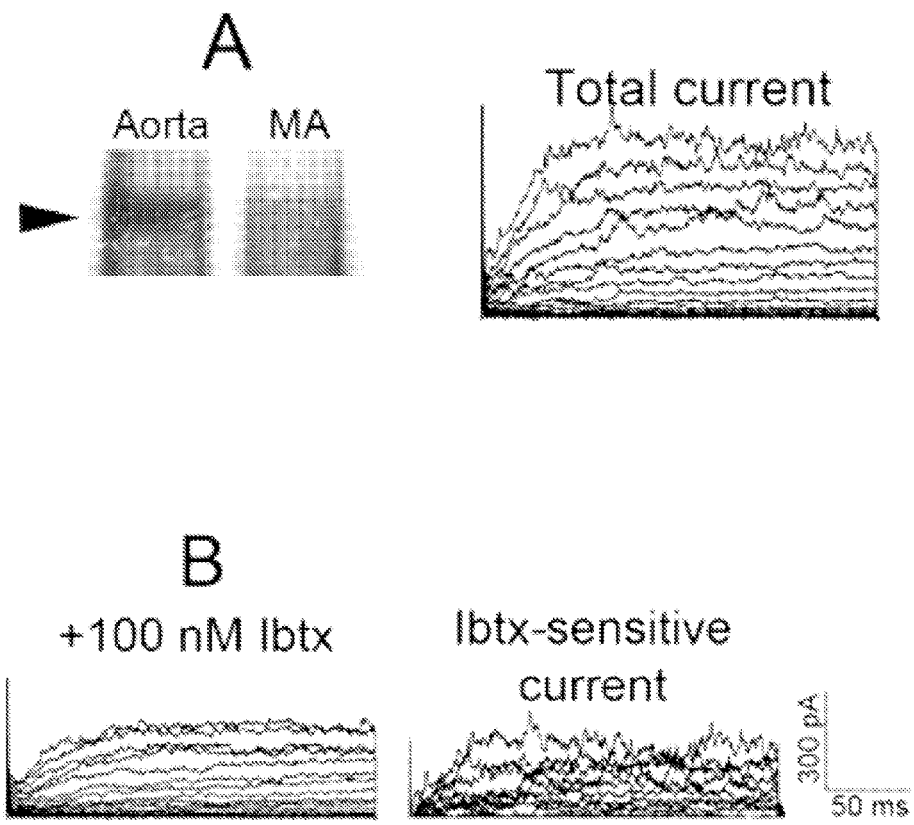

FIG. 6 depicts a photograph and graphs showing the presence of BKα in mouse aorta and mesenteric arteries. A) Western blot detection of BKα (~125 kD) in mouse aorta and mesenteric arteries (MA). B) Whole-cell K+ current in a mouse mesenteric current in VSMCs from the mouse VSMC before (left trace), and after (middle trace) the addition of the BK channel mesentery, a vascular bed involved blocker, iberiotoxin (100 nmol/L Ibtx). The difference between the two traces was computed digitally to isolate the Ibtx-sensitive BK current (right trace).

Figure 7:
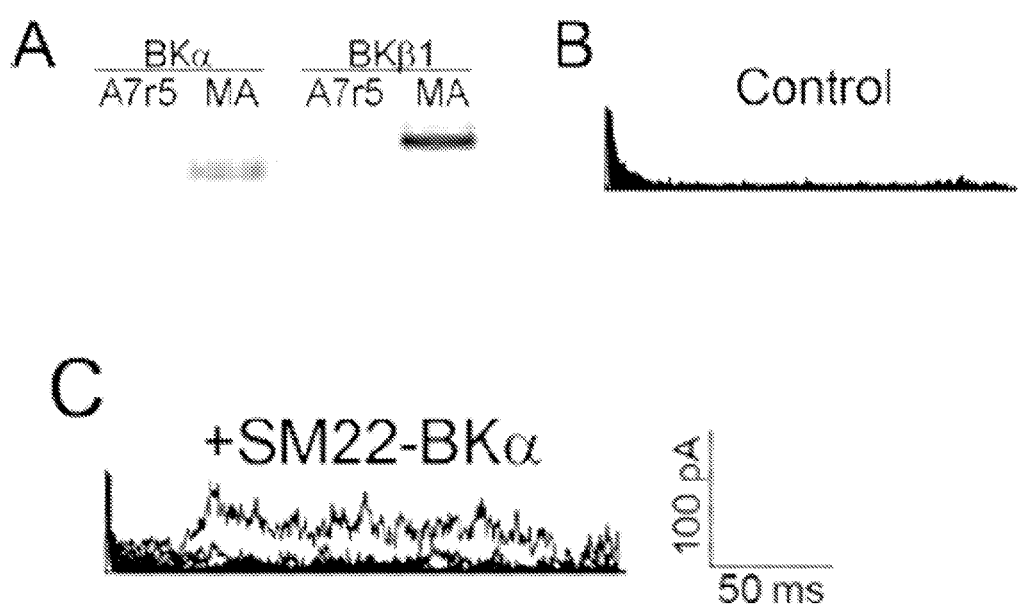

FIG. 7 depicts illustrations showing expression data. A) PCR amplification revealed the absence of BKα and BKβ1 mRNAs in A7r5 cells. Rat mesenteric arteries (MA) were used as a positive expression control. B) Voltage pulses from a holding potential of −70 mV to +50 mV failed to elicit K+ current in A7r5 cells. C) However, A7r5 cells transfected with SM22-BKα displayed K+ current.

Figure 8:
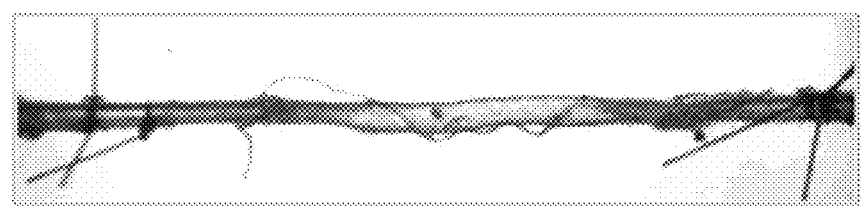
Figure 8:
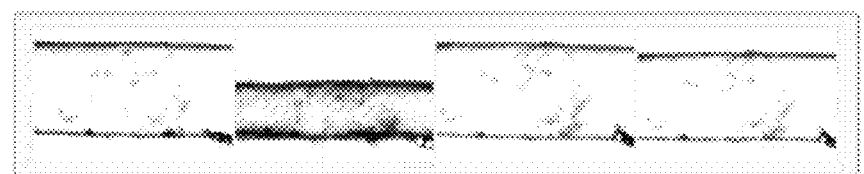
Figure 8:
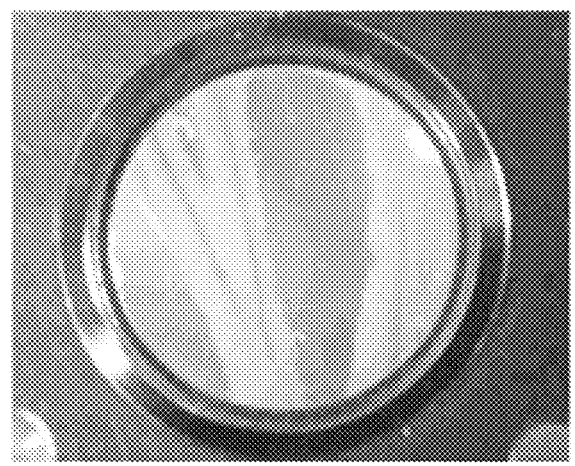

FIG. 8 depicts photographs showing how vascular reactivity assays will compare the dilator function of BK channels between arteries of normotensive mice, hypertensive mice, and mice treated with the AAV/BKα gene, using: A and B) Isolated, cannulated mesenteric arteries. The dilator influence of BK channels will be blocked by iberiotoxin (Ibtx). C) Similar diameter responses will be assessed in the intact mesenteric vascular bed using intravital video microscopy (IVVM).

Figure 9:
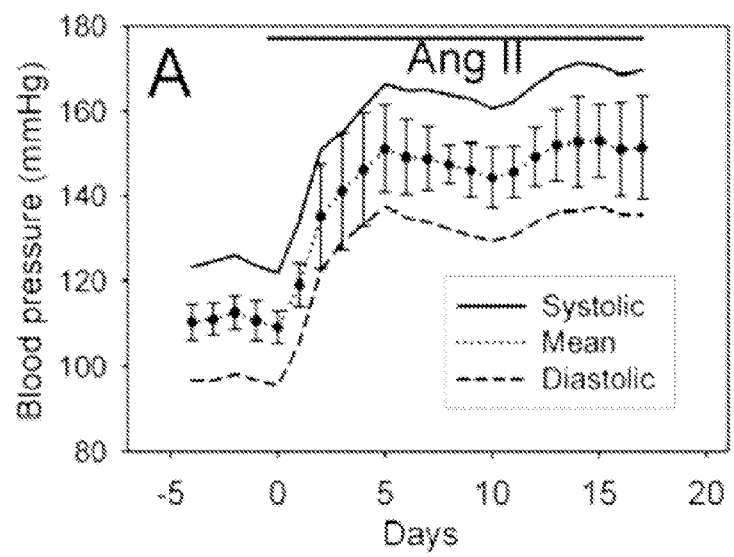
Figure 9:
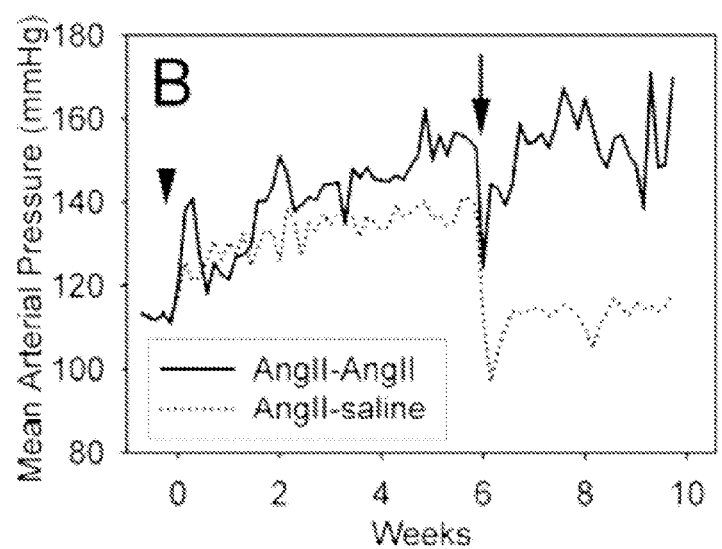
Figure 9:
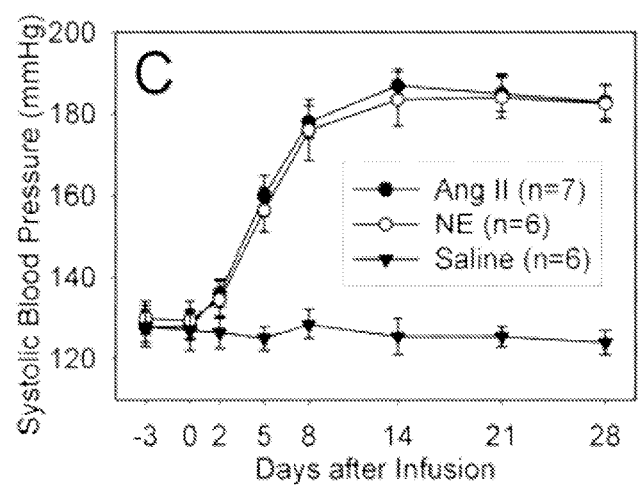

FIG. 9 depicts graphs showing blood pressure of mice exposed to angiotensin II. A) Daily averages of systolic, mean, and diastolic pressure measured by biotelemetry. Ang II minipumps (2 μg/kg/min) were implanted on Day 0. Error bars (SD, n=5). B) Mean arterial pressure from two mice measured by biotelemetry. Ang II minipumps inserted on Day 0 (arrowhead) were exchanged after six weeks (arrow) with a second Ang II (top trace) or a saline minipump (lower trace). C) Systolic blood pressure measured by tailcuff. Ang II (2 μg/kg/min), NE (4 μg/kg/min), or saline minipumps were implanted on Day 0. Error bars (SEM, n=6, 7).

Figure 10:

FIG. 10 depicts a photograph of the expression of the vector. DNA extracted from mesenteric arteries from each group of mice was probed for AAV/BKα to confirm AAV-mediated gene delivery.

Figure 11:
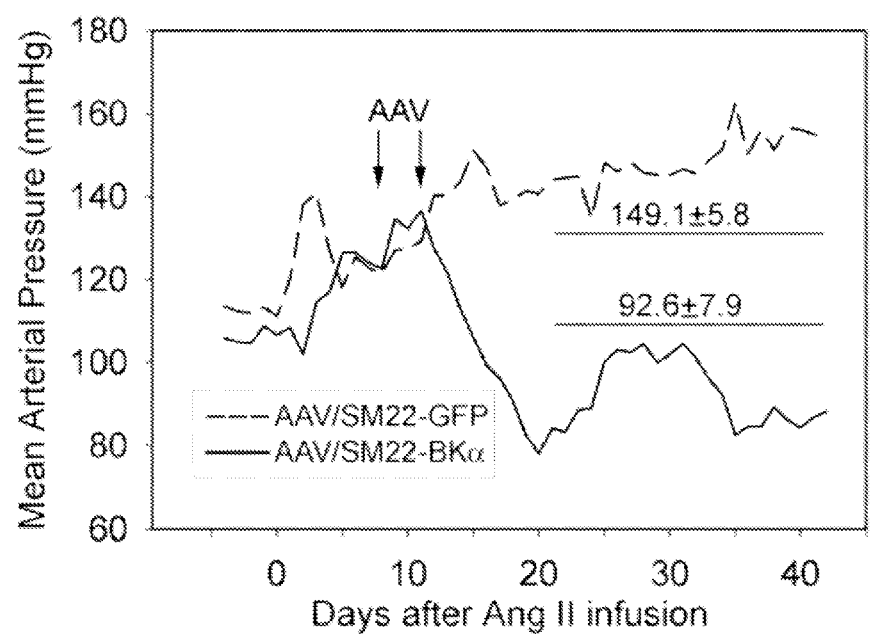

FIG. 11 depicts a graph showing Ang II-induced hypertension was not attenuated in mice injected with 2 doses of AAV/SM22-GFP $5\times10^{10}$ vp/kg; 3 days apart. However, a sustained reduction in blood pressure was recorded by telemetry in a similar Ang II-infused hypertensive mouse injected with the same viral dose of AAV/SM22-BKα.

DETAILED DESCRIPTION OF THE INVENTION

The present invention provides compositions and methods for the expression of a calcium-activated potassium channel in smooth muscle cells. In particular, the present invention provides a vector comprising a smooth muscle promoter operably linked to a nucleic acid encoding a calcium-activated potassium channel.

I. Composition Comprising a Vector

One aspect of the present invention is a composition comprising a vector for expressing a calcium-activated potassium channel in a smooth muscle cell. In various configurations, the vector may comprise a smooth muscle specific promoter operably linked to a nucleic acid sequence encoding a calcium-activated potassium channel. A nucleic acid sequence and a promoter are "operably linked" if the promoter sequence effectively controls transcription of the nucleic acid sequence.

The term "vector," as used herein, refers to any nucleic acid capable of transforming target cells and expressing an inserted calcium-activated potassium channel nucleic acid or fragment of a calcium-activated potassium channel nucleic acid. The vector may be autonomously replicating or not, double-stranded or single-stranded, or encased in a viral capsid or not. Vectors of the present invention include viruses comprising capsid and nucleic acid, viral nucleic acid without capsid, DNA plasmids, linear DNA molecules and linear or circular RNA molecules. Vectors of the present invention include those vectors derived from retroviruses, adenovirus, adeno-associated virus, SV40 virus, or herpes virus. An adeno-associated virus (AAV) of the present invention may include any sub-type of adeno-associated virus capable of transducing a genetic element. In various embodiments of the present invention, the vector comprises an AAV vector. AAV vectors are known in the art, and may include, for instance, a vector, or a variant thereof, disclosed in U.S. Pat. No. 5,139,941, hereby incorporated by reference in its entirety.

(a) Promoter

A vector of the invention typically comprises a smooth muscle cell specific promoter. A "promoter" or "promoter sequence," as used herein, is a nucleic acid regulatory region capable of binding RNA polymerase in a cell and initiating transcription of a downstream (3' direction) coding sequence. For purposes of defining the present invention, a promoter sequence extends upstream (5' direction) from the transcription start site to include the minimum number of bases or elements necessary to initiate transcription at levels detectable above background. In some instances, elements of a promoter may be found downstream (3') of the transcription initiation site. Within the promoter sequence may be found a transcription initiation site, as well as protein binding domains (consensus sequences) responsible for the binding of cis and trans acting proteins and RNA polymerase. Eukaryotic promoters often, but not always, contain "TATA" boxes and "CAT" boxes.

"Smooth muscle cell specific," as used herein, means that the promoter preferentially initiates transcription in smooth muscle cells as opposed to other cell types. In an exemplary embodiment, the promoter has detectable activity only in smooth muscle cells. A promoter of the invention may be from a mammal such as a rodent, a non-human primate, a companion animal, a livestock animal, or a human. Non-limiting examples of rodents may include mice, rats, and guinea pigs. Non-limiting examples of companion animals may include dogs and cats. Non-limiting examples of a livestock animal may include swine, cattle, or goats.

A promoter may be constitutive or may be regulatable. Non-limiting examples of a regulatable promoter may include promoters that require activators to initiate transcription, or alternatively, repressors to stop transcription. For instance, the tetracycline regulatable promoter may be used (i.e. the $tet_{on}/tet_{off}$ system). Such regulatable promoters are known in the art.

In some embodiments, a promoter of the invention may be derived from a nucleic acid sequence specifically expressed in a smooth muscle cell. For instance, the promoter may be selected from the group comprising the SMMHC (smooth muscle myosin heavy chain, 16 kb) promoter, the FRNK (autonomously expressed carboxyl-terminal region of focal adhesion kinase, 15 kb) promoter, the CRP1 (Cysteine-Rich Protein 1, 5 kb) promoter, or the SM22α promoter. In one embodiment, the promoter may be a SM22α promoter. As used herein, "SM22α promoter" refers to the region immediately upstream (5') of the structural SM22α gene that controls expression of that gene. In some instances, the promoter may comprise the region of up to 50, 100, 500, 1,000, 1,500, 2,000 or even up to about 5,000 bases immediately upstream of the translational start site of the SM22α gene. An SM22α promoter may also be described as an isolated nucleic acid segment comprising a contiguous sequence of bases from the SM22α gene such as bases −445 to +61, or such as a sequence of −441 to +41 bases from the transcription start site. The designations of −445 to +61 and the like indicate the position of a base relative to the transcriptional start site (+1).

Additionally, a promoter of the present invention includes any substantially homologous nucleic acid sequence that may be truncated, mutated, or any other variant of a promoter so long as the promoter remains operable and retains specificity for smooth muscle cell expression. Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., DNA Cloning, Vols. I & II; Nucleic Acid Hybridization.

In one embodiment, the promoter may comprise SEQ ID NO:1. SEQ ID NO. 1 represents a 507 nucleotide sequence corresponding to a mouse SM22α promoter. Alternatively, the promoter may comprise SEQ ID NO:2. SEQ ID NO:2 represents a 499 nucleotide sequence corresponding to a variant of a mouse SM22α promoter. In another embodiment, a promoter of the invention may have 75%, 80%, 85%, 90%, 91%, 92%, 93%, 94%, 95%, 96%, 97%, 98%, or 99% homologous to SEQ ID NO:1 or SEQ ID NO:2, so long as the promoter remains operable and retains specificity for smooth muscle cell expression. In yet another embodiment, a promoter may be a fragment of SEQ ID NO:1 or SEQ ID NO:2 that remains operable and retains specificity for smooth muscle cell expression.

In some embodiments, the promoter may be a human SM22α promoter. SEQ ID NO. 9 comprises a nucleotide sequence corresponding to the human SM22α coding sequence and smooth muscle specific promoter, which may be found as GenBank Accession No. D84342. A human SM22α promoter may include regulatory elements found 5' to the ATG codon, including elements such as two CArG/SRF-boxes and two GC-box/Sp 1 binding sites present at bp −147 and −274, and at by −233 and −1635, respectively.

In certain embodiments, a smooth muscle cell promoter may be a variant of a parent promoter that is not itself specific for a smooth muscle cell. For instance, a promoter may be altered, or varied, so that it is specific for a smooth muscle cell. For example, the smooth muscle cell promoter may be a variant of the cardiac myosin heavy chain promoter. In particular, the promoter may comprise the MusB promoter. Unlike the parent promoter, MusB is smooth muscle cell specific. Hence, in one embodiment, the promoter comprises SEQ ID NO:3. SEQ ID NO:3 represents a 246 nucleotide sequence corresponding to the mouse smooth muscle specific promoter MusB.

Additionally, a promoter of the present invention includes any substantially homologous nucleic acid sequence that may be truncated, mutated, or any other variant of the MusB promoter so long as the promoter remains operable and retains specificity for smooth muscle cell expression. Substantially homologous, as used herein, is defined above. For instance, in one embodiment, a promoter of the invention may have 75%, 80%, 85%, 90%, 91%, 92%, 93%, 94%, 95%, 96%, 97%, 98%, or 99% homologous to SEQ ID NO:3, so long as the promoter remains operable and retains specificity for smooth muscle cell expression. In another embodiment, a promoter may be a fragment of SEQ ID NO:3 that remains operable and retains specificity for smooth muscle cell expression.

In each of the above embodiments, a promoter may be smaller than the sequences specifically identified herein thereby operating as a minimal sequence required for constitutive smooth muscle cell transcription. Certain portions of sequences in a promoter may be required for spacing of the cis acting elements and any sequence that does not impart deleterious structural properties may be substituted for those spacer regions so long as the spacing remains substantially intact to allow the cis acting elements to function. All such promoters would be encompassed by the present invention.

In an exemplary embodiment, a promoter of the invention is of a length suitable for use in an AVV vector.

(b) Calcium-Activated Potassium Channel

A vector of the invention also typically comprises a nucleic acid sequence encoding a calcium-activated potassium channel. As used herein, "calcium-activated potassium channel" refers to a protein capable of forming an ion-conducting pore. Suitable calcium-activated potassium channels may include high conductance voltage-activated potassium channels, such as "BK channels." In exemplary embodiments, a vector may comprise a subunit of a BK channel. A BK channel is typically composed of an α subunit (BKα) and a β subunit (BKβ). In one embodiment, a vector of the invention comprises a BKβ subunit. In another embodiment, a vector of the invention comprises a BKβ subunit. A calcium-activated potassium channel of the invention may be from a mammal such as a rodent, a non-human primate, a companion animal, a livestock animal, or a human. Non-limiting examples of rodents may include mice, rats, and guinea pigs. Non-limiting examples of companion animals may include dogs and cats. Non-limiting examples of a livestock animal may include swine, cattle, or goats.

In one embodiment, a nucleic acid sequence encoding a calcium-activated potassium channel may be, for example, SEQ ID NO.:4. SEQ ID NO.:4 is a nucleotide sequence that comprises a coding sequence for a BKα protein, which may be found in GenBank under Accession No. U09383. In various embodiments of the present invention, the vector comprising a calcium-activated potassium channel may comprise the entire nucleotide sequence of SEQ ID NO.: 4. Alternatively, the vector may comprise only the coding sequence of SEQ ID NO.: 4 or a fragment thereof.

In another embodiment, a nucleic acid sequence encoding a calcium-activated potassium channel may be, for example, SEQ ID NO.:6. SEQ ID NO.:6 is a nucleotide sequence that comprises the coding sequence for a BKα protein, which may be found in GenBank under Accession No. NM_002247. In various embodiments of the present invention, the vector comprising a calcium-activated potassium channel may comprise the entire nucleotide sequence of SEQ ID NO.:6. Alternatively, the vector may comprise only the coding sequence of SEQ ID NO.: 6 or a fragment thereof.

In yet another embodiment, a nucleic acid sequence encoding a calcium-activated potassium channel may be, for example, SEQ ID NO.: 7. SEQ ID NO.: 7 is a nucleotide sequence that comprises the coding sequence for a BKα protein, which may be found in GenBank under Accession No. NM_001014797. In various embodiments of the present invention, the vector comprising a calcium-activated potassium channel may comprise the entire nucleotide sequence of SEQ ID NO.: 7. Alternatively, the vector may comprise only the coding sequence of SEQ ID NO.: 7 or a fragment thereof.

In still another embodiment, a nucleic acid sequence encoding a calcium-activated potassium channel may be, for example, SEQ ID NO.:8. SEQ ID NO.:8 is a nucleotide sequence that comprises the coding sequence for a BKα protein, which may be found in GenBank under Accession No. NM_002247. In various embodiments of the present invention, the vector comprising a calcium-activated potassium channel may comprise the entire nucleotide sequence of SEQ ID NO.:8. Alternatively, the vector may comprise only the coding sequence of SEQ ID NO.: 8, or a fragment thereof.

A calcium-activated potassium channel sequence of the present invention may also include any substantially homologous nucleic acid sequence that may be truncated, mutated, or any other variant of a calcium-activated potassium channel so long as the channel remains operable, i.e. forms an ion-conducting pore. Substantially homologous, as used herein, is defined above. For instance, in one embodiment, a calcium-activated potassium channel of the invention may have 75%, 80%, 85%, 90%, 91%, 92%, 93%, 94%, 95%, 96%, 97%, 98%, or 99% homology to SEQ ID NO:4, SEQ ID NO:6, SEQ ID NO:7, or SEQ ID NO:8, so long as the channel remains operable. In another embodiment, a calcium-activated potassium channel may be a fragment of SEQ ID NO:4, SEQ ID NO:6, SEQ ID NO:7, or SEQ ID NO:8 that remains operable.

(c) Combinations

A vector of the invention may comprise various combinations of a smooth muscle promoter operably linked to a calcium-activated potassium channel. For instance, a vector may comprise a combination listed in Table A.

TABLE A

| PROMOTER | CALCIUM-ACTIVATED POTASSIUM CHANNEL |
|---|---|
| SEQ ID NO: 1 | SEQ ID NO: 4 |
| SEQ ID NO: 1 | SEQ ID NO: 6 |
| SEQ ID NO: 1 | SEQ ID NO: 7 |
| SEQ ID NO: 1 | SEQ ID NO: 8 |
| SEQ ID NO: 2 | SEQ ID NO: 4 |
| SEQ ID NO: 2 | SEQ ID NO: 6 |
| SEQ ID NO: 2 | SEQ ID NO: 7 |

TABLE A-continued

| PROMOTER | CALCIUM-ACTIVATED POTASSIUM CHANNEL |
|---|---|
| SEQ ID NO: 2 | SEQ ID NO: 8 |
| SEQ ID NO: 3 | SEQ ID NO: 4 |
| SEQ ID NO: 3 | SEQ ID NO: 6 |
| SEQ ID NO: 3 | SEQ ID NO: 7 |
| SEQ ID NO: 3 | SEQ ID NO: 8 |
| SEQ ID NO: 9 | SEQ ID NO: 4 |
| SEQ ID NO: 9 | SEQ ID NO: 6 |
| SEQ ID NO: 9 | SEQ ID NO: 7 |
| SEQ ID NO: 9 | SEQ ID NO: 8 |

In particular, the vector may comprise SEQ ID NO.: 5, which is a 9,188 nucleotide sequence comprising part of an AAV genome, the smooth muscle specific promoter sequence of SEQ ID NO.: 1 and a nucleic acid encoding a calcium-activated potassium channel as represented by SEQ ID NO.: 4.

(d) Pharmaceutical Composition

A vector of the invention may comprise a pharmaceutical composition. In some embodiments, the compositions may comprise pharmaceutically acceptable excipients. Examples of suitable excipients may include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The compositions may additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention may be formulated so as to provide quick, sustained or delayed release of the active ingredient after administration to a subject by employing procedures known in the art.

Injectable preparations of a composition of the invention, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally or intrathecally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Formulations for administration of the composition may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

II. Methods

The present invention further comprises a method of regulating the blood pressure of a mammal. In certain embodiments, the method comprises administering to said mammal a vector comprising a smooth muscle specific promoter operably linked to a nucleic acid sequence encoding a calcium-activated potassium channel. Accordingly, the smooth muscle specific promoter may be selected from the group consisting of SEQ ID NO.: 1, SEQ ID NO.: 2, and SEQ ID NO.: 3. The nucleic acid sequence encoding a calcium-activated potassium channel may be, for example, SEQ ID NO.: 4. In particular embodiments, a vector that is useful for the present method may comprise an AAV vector. Specifically, the vector may comprise SEQ ID NO.: 5. The method of the present embodiment may be used to regulate the blood pressure of a mammal, including for example, the blood pressure of a rodent, a non-human primate, a companion animal, a livestock animal, or a human. Non-limiting examples of rodents may include mice, rats, and guinea pigs. Non-limiting examples of companion animals may include dogs and cats. Non-limiting examples of a livestock animal may include swine, cattle, or goats.

In a further embodiment of the present invention, a method of expressing a calcium-activated potassium channel in a smooth muscle cell is disclosed. Such a method comprises contacting the smooth muscle cell with a vector comprising a smooth muscle specific promoter operably linked to a nucleic acid sequence encoding a calcium-activated potassium channel. The smooth muscle specific promoter may be selected from the group consisting of SEQ ID NO.: 1, SEQ ID NO.: 2, SEQ ID NO.: 3 and SEQ ID NO:9. Additionally, the nucleic acid sequence encoding a calcium-activated potassium channel may be SEQ ID NO.: 4. In some modes of the present embodiment, the vector may comprise an AAV vector, and in specific modes, the vector may comprise SEQ ID NO.:5. The promoter and the calcium-activated potassium channel may be a mammalian, and in particular, may be from a rodent, a non-human primate, a companion animal, a livestock animal, or a human. Non-limiting examples of rodents may include mice, rats, and guinea pigs. Non-limiting examples of companion animals may include dogs and cats. Non-limiting examples of a livestock animal may include swine, cattle, or goats.

Definitions

A DNA "coding sequence" is a double-stranded DNA sequence which is transcribed and translated into a polypeptide in vivo when placed under the control of appropriate regulatory sequences. The boundaries of the coding sequence are typically determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

The term "high stringency" means DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

A cell has been "transformed" by exogenous or heterologous DNA when such DNA has been introduced inside the cell. The transforming DNA may or may not be integrated (covalently linked) into the genome of the cell.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Reduction of Blood Pressure

Figure 1:
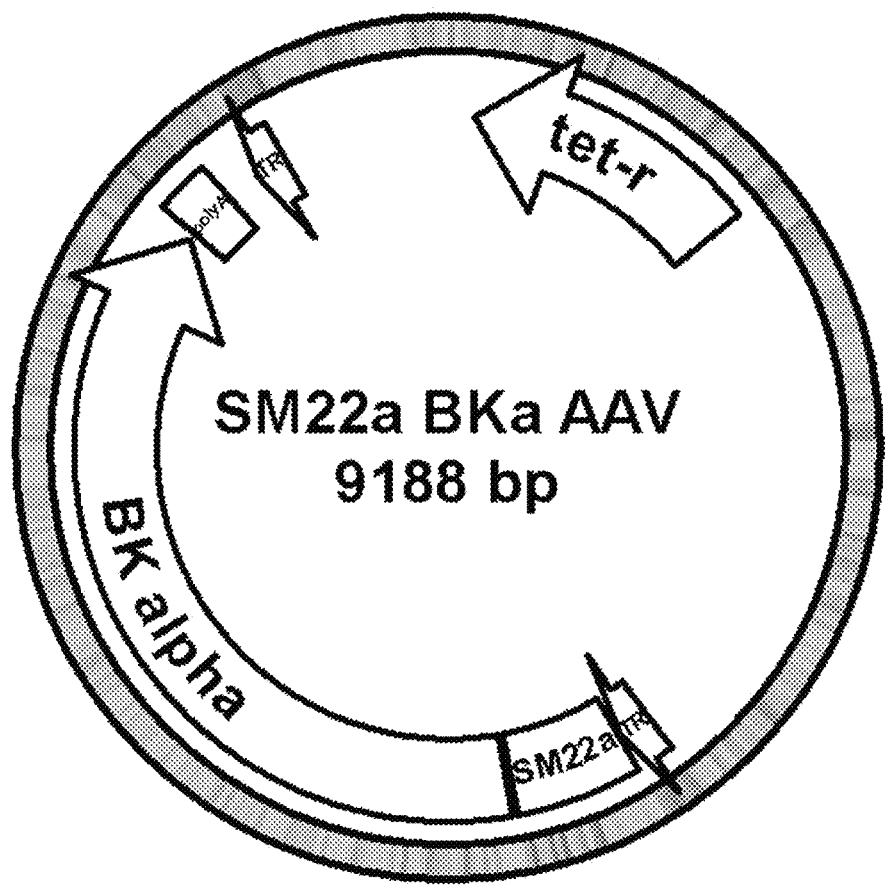
FIG. 1 depicts an illustration of a map of a vector of the present invention.

The AAV delivery of pore-forming, BKα-subunits into the vascular smooth muscle cells (VSMCs) of resistance arteries reduces blood pressure in hypertensive mice but does not affect resting blood pressure levels. The present inventors have constructed the AAV vector with the mouse BK transgene (mSlo) using either of two smooth muscle specific promoters, including a truncated form of the SM22α promoter that shows VSMC specificity (see FIG. 1 and SEQ ID NO.: 5). Also, the present inventors have constructed an AAV vector using a newly designed "MusB" promoter derived from the cardiac myosin heavy chain promoter that prefers VSMC transgene expression.

The antihypertensive effect of two AAV vectors, AAV/MusB-BKα and AAV/SM22BKα, were evaluated using tail-cuff plethysmography. These studies provided the evidence that AAV-mediated delivery of BKα could profoundly reduce high blood pressure in hypertensive mice. The AAV vectors were administered by tail vein injection prior to inducing hypertension by Ang II infusion in C57BL/6J mice.

Figure 2:
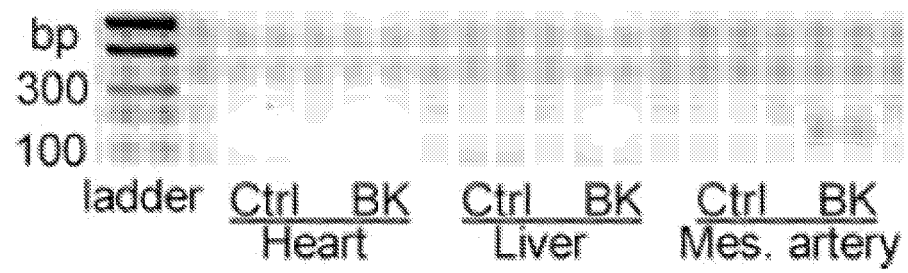
FIG. 2 depicts a photograph illustrating PCR amplification of the BKα transgene. Samples were taken from heart, liver, and mesenteric arteries of mice 6 weeks after injecting AAV/MusB-GFP (Control, Ctrl) or AAV/SM22-BKα (BK). Only the mesenteric artery showed PCR product corresponding to mRNA of the BKα transgene.
Figure 3:
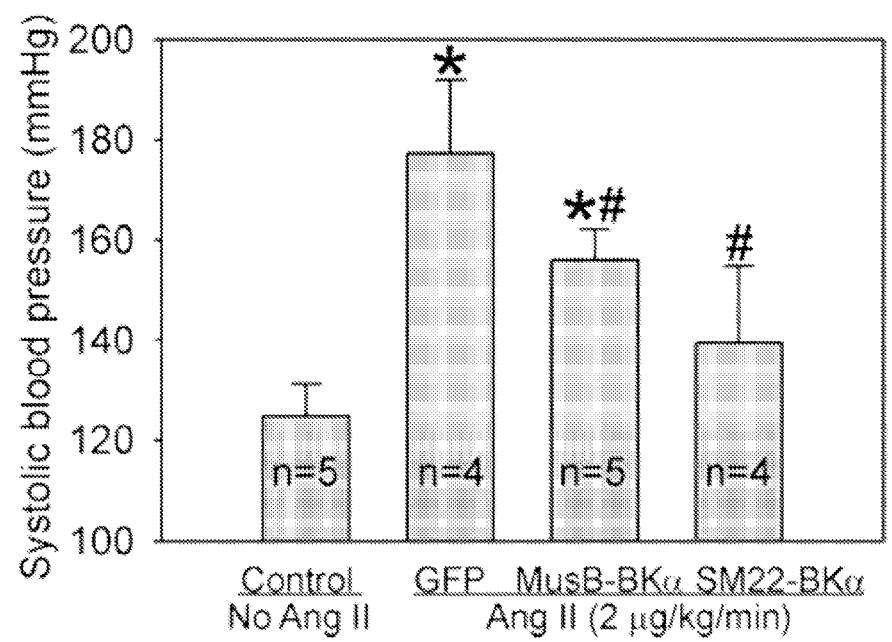
FIG. 3 depicts a graph showing a reduction in blood pressure. SBP was averaged during a 2 week interval in four groups of mice (n=4-5 each). Control mice (control) were not injected with AAV or infused with Ang II. The other 3 groups of mice received tail vein injections of either AAV/MusB-GFP ($10^{11}$ vp/kg), AAV/MusB-BKα ($10^{10}$ vp/kg) or AAV/

As a first strategy, the virus was allowed to fully express MusB-BKα or SM22-BKα for 3 weeks to determine if the mature expression of the therapeutic BKα transgene could blunt Ang II-induced hypertension. Two different doses of virus particles (vp) were evaluated. Mice were injected with either AAV/MusB-BKα ($10^{10}$ vp/kg; n=5), AAV/SM22-BKα ($10^{11}$ vp/kg; n=4), or AAV/MusB-GFP as a control vector ($10^{11}$ vp/kg; n=4). Subsequently, PCR amplification of the AAV/BKα DNA fragment confirmed a smaller amount of DNA corresponding to the BKα transgene in the mesenteric arteries of mice injected with AAV/MusB-BKα compared to AAV/SM22-BKα, corresponding to the 10-fold less AAV/MusB-BKα virus particles injected (FIG. 2 and FIG. 10). Three weeks after AAV injection, Ang II (2 μg/kg/min) was infused by osmotic minipump for one week to establish hypertension (as shown in FIG. 9A), and systolic blood pressure (SBP) was monitored by tail cuff every weekday for 2 weeks. One day's measurement consisted of 5 readings from each animal done as a two-person, single-blind experiment. The ten-day average value was assigned to each animal and statistical analysis was done on those values (n=4 or 5). Both AAV/BKα groups had significantly lower SBP than mice injected with the control vector, AAV/MusB-GFP, which showed an average SBP of 177±15 mm Hg (FIG. 3 and FIG. 3). In contrast, the SBP of mice injected with AAV/MusB-BKα ($10^{10}$ vp/kg) was 156±6 mm Hg, and the SBP of mice injected with AAV/SM22-BKα ($10^{11}$ vp/kg) averaged 140±15 mm Hg. All animals appeared healthy, and showed similar weights. To our knowledge, these findings provide the first evidence that AAV delivery using smooth muscle-specific promoters to deliver a K+ channel gene to arterial VSMCs can profoundly blunt the development of high blood pressure in hypertensive animals.

Example 2

Promoters

The SM22α promoter is one of the few documented smooth muscle-specific promoters that preferentially expresses genes in arterial VSMCs compared to other cell types, and even compared to other types of smooth muscle cells including visceral or venous. The truncated SM22α is the only form that is small enough in size (445 bp) to be packaged into AAV with our therapeutic gene, BKα. However, a putative smooth muscle-specific promoter, "MusB", was recently discovered that also is small enough in size (245 bp) to be used in AAV vectors. The MusB promoter was generated during a study to make small, AAV-friendly, muscle-active promoters. The promoter region of the full-length cardiac a myosin heavy chain (GenBank accession No. Z20656) was truncated by removing the putative "enhancer" element (nucleotide 4120-4321). The resulting MusB promoter (FIG. 4A) is 245 bp in length and has preferential activity in cultured VSMCs compared to cardiac cells. Unlike SM22α, the MusB promoter does not have a perfect CArG box element (CCWWWWWWGG, where W=A or T) directed by the serum response factor that is evolutionarily conserved for SMC-specific promoter activity. However, MusB has an imperfect CArG box (CCAAATTTAG, where A should be G), and there are 1216 permutations of the CArG box that are regarded as functional. Indeed, 24 hours after transfection of the luciferase gene with the MusB promoter, primary cultures of rat aortic VSMCs show about 20-fold more activity than primary cultures of neonatal rat cardiac myocytes (FIG. 4B). Because of the high activity of the MusB promoter in VSMCs, and the paucity of small, smooth muscle-specific promoters available for AAV-mediated delivery of target genes to the vasculature, the efficacy of the two smooth muscle-specific promoters, SM22α and MusB, will be compared for AAV transduction of genes into arterial VSMCs. For clarity, and to avoid confusion of SM22α with BKα in shared constructs, the SM22α promoter is referred to only as "SM22" in the remaining text.

Four AAV plasmid constructs containing the truncated SM22 promoter or the new MusB promoter and the mouse BKα gene or the gene for green fluorescent protein (GFP) were prepared (FIG. 4C). The large size (3.5 kb) of the BKα gene approaches the insert gene size limit for the AAV vector. Thus GFP requires a separate construct for studies designed to evaluate gene expression conferred by AAV/SM22 or AAV/MusB. From these plasmids, AAV (serotype 2) virus stocks were generated and the titer estimated at ~$10^9$ virus particles per milliliter (vp/ml) by quantitative PCR. These constructs and similar virus stocks will be referred to by promoter and gene, for example, AAV/SM22BKα. A myc tag may also be added to the AAV/SM22-BKα and AAV/MusB-BKα constructs to enhance detection of the BKα protein in the arterial wall and in single VSMCs.

Example 3

The SM22 and MusB Promoters Drive Gene Expression in Arterial VSMCs

In early experiments, evidence was obtained that the SM22 promoter can achieve long-term gene expression in arterial VSMCs in vivo. As a prelude to these studies, A7r5 cells (an embryonic rat aortic VSMC line) were transfected with plasmids encoding SM22-GFP and MusB-GFP (2 μg/$10^5$ cells) to verify that both promoters have activity in these cultured VSMCs. Indeed, GFP associated with both plasmids was detected at 72 hours after transfection at qualitatively similar levels of expression in the A7r5 cells (FIG. 5A). Subsequently, we injected $10^{11}$ vp/kg AAV/SM22-GFP into the tail vein of control C57BL/6J adult mice to determine (as a starting point) if our AAV construct, using the best characterized smooth muscle-specific promoter, SM22, could achieve long-lasting gene expression in VSMCs in vivo. Indeed, 10-μm frozen sections of the aorta collected 9 weeks after the mice were injected with AAV/SM22-GFP showed clear GFP expression in the VSMCs composing the aortic medial layers (FIG. 5B, white arrows), which are situated between the elastic fibers that show high auto fluorescence (FIG. 5B, yellow arrowheads). To our knowledge, this is the first use of a smooth muscle-specific promoter to enact long-lasting expression of a gene in VSMCs using AAV-mediated delivery. Standard PCR of the cDNA using a primer pair designed to amplify only the BKα transgene but not the endogenous BKα gene (forward primer: TTCGGCTTGGGTCGACTCT-TAGAA (SEQ ID NO:10) reverse primer: TATGATGAGCG-CATCCATCTTGGG (SEQ ID NO:11) revealed that only mesenteric arteries from AAV/SM22-BKα-injected mice showed detectable levels of message. The BKα message was not transcribed in heart or liver, confirming that SM22 does not exert promoter activity in nonvascular tissues. An agarose gel comparing transduced BKα amplified product corresponding to mRNA from AAV/MusB-GFP and AAV/SM22-BKα is shown in FIG. 2.

The pore-forming structure of the BK channel in VSMCs is presumed to represent a tetramer composed of four α subunits, which associate with ancillary β1 subunits to confer $Ca^{2+}$ sensitivity to the channel complex. Thus, both subunits (α and β1) are thought to be required for normal physiological function. Since we propose to deliver only the BKα subunit to VSMCs by AAV, it is possible that the availability of β1 will limit the number of fully functional BK channels. Thus, one goal of this experiment was to verify that AAV delivery of BKα enhances BK channel-mediated K+ current in the arterial VSMCs of the treated animals, and to confirm that BK channels show normal $Ca^{2+}$-dependent activation indicative of α4β4 complex formation. In this regard, arterial BKα DNA, mRNA and protein expression was evaluated. In Western blots, the BK subunit is detected as a 125 kD band (FIG. 6A).

BK channel current in VSMCs from the mouse mesentery, a vascular bed involved in blood pressure regulation will be scrutinized. First, we will characterize the whole-cell properties of BK current in VSMCs of 2nd order mesenteric arteries from untreated C57BL/6J mice. After profiling the density and properties of the native BK channels, the BK current in the VSMCs of hypertensive mice treated with AAV/SM22-BKα or AAV/MusB-BKα antihypertensive therapy will be examined using previously published protocols. A sample protocol is shown in FIG. 6B in a freshly isolated mesenteric VSMC from an untreated C57BL/6J mouse. Voltage-elicited K+ current (left trace) was reduced by the well characterized BK channel blocker, iberiotoxin (Ibtx, middle trace). Other voltage-elicited K+ channel currents also were evident as the Ibtx-resistant residual current. Digital subtraction was used to isolate the Ibtx-sensitive component of BK current from total K+ current (right trace). It is expected that AAV delivery of BKα will increase the density of Ibtx-sensitive current attributed to the BK channel, and further patch-clamp studies will evaluate if the transduced BK channel retains normal voltage and $Ca^{2+}$-sensitivity.

Studies were initiated to confirm that the MusB-BKα and SM22-BKα plasmids encode functional BK channels in VSMCs. For these studies, a VSMC line was identified that did not express native BK channels. Notably, a standard non-smooth muscle expression systems (ie, HEK 293) could not be used, because MusB-BKα and SM22-BKα plasmids contain a smooth muscle-specific promoter. Fortunately, screening efforts revealed that A7r5 cells do not express voltage-gated K+channels. Indeed, the BK α and β transcripts that are readily detected in freshly isolated mesenteric arteries (FIG. 7A, MA) are not expressed in A7r5 cells, a neonatal rat aortic cell line. A7r5 cells also lack voltage-dependent K+ current (n=9) (FIG. 7B). It has been observed that patch-cell-specific promoters show activity in VSMCs that appears to result in functional channel proteins.

Example 4

Evaluation of BK Channel Dilator Function In Vitro and In Vivo

To verify that the antihypertensive effect of BKα gene delivery is associated with an enhanced dilator influence of BK channels, in vitro and in vivo dilator assays will be used. Studies will focus on the mesenteric circulation, a vascular bed that offers a number of advantages. First, the mesenteric circulation plays a central role in blood pressure regulation. Second, the web of mesenteric arcade arteries provides enough vascular tissue from only several mice for DNA, RNA and protein analyses, vessel reactivity studies, and patch-clamp studies. Third, the mesenteric circulation is accessible for intravital video microscopy (IVVM) to assess BK channel-mediated vasodilation in vivo in an anesthetized mouse. Thus, although there is the capability to study other vascular beds if the need arises the mesenteric circulation is conceptually and technically suited to the planned studies. In vitro vascular reactivity studies will use isolated, cannulated mesenteric arteries (FIG. 8A). The dilator function of the BK channel will be evaluated at 3 levels of intramural pressure (60 mm Hg, 100 mm Hg, and 140 mm Hg). A sample protocol in a mouse mesenteric artery perfused at 100 mm Hg is shown in FIG. 8B. After equilibration to establish resting tone (panel 1; internal diameter=127 μm), maximal depolarization-induced contraction was elicited by 60 mmol/L KCl (panel 2). After washout of KCl to re-establish resting diameter (panel 3), iberiotoxin (100 nmol/L Ibtx) was added to block BK channel-mediated dilation. The loss of BK channel-mediated vasodilation caused a diameter reduction that was equal to 16% of the maximal contraction to KCl (panel 4). These data suggest that the BK channel contributes only a small dilator influence to the resting tone of small mesenteric arteries at physiological perfusion pressures. The vasoconstrictor response to Ibtx is expected to be accentuated in arteries of mice transduced with the BKα gene. Similarly, IVVM will be used to compare the vasodilator influence of the BK channel between the mesenteric circulations of control mice and mice treated with AAV/SM22-BKα or AAV/MusB-BKα. In these mice, the mesentery is pulled through a midline incision and placed in an observation chamber on the stage of an upright microscope for on-line recording of arterial diameters in vivo (FIG. 8C). The level of BK channel-mediated vasodilation can be assessed using iberiotoxin as described above for the perfused artery preparation. A similar technique has been used for recording in situ membrane potential and diameters in the mesenteric circulation of anesthetized rats and also for monitoring the reactivity of the renal circulation in mice. This technique will be adapted to the mouse mesenteric circulation, as shown in FIG. 7C.

Example 5

Mouse Models of Hypertension and Biotelemetry Measurement

To evaluate the antihypertensive effect of AAV-mediated delivery of BKα, two mouse models of hypertension will be used. Surgical procedures will be performed, and heart rate and blood pressure will be monitored using biotelemetry. Chronic hypertension will be induced in C57BL/6J mice by implanting osmotic minipumps for infusion of angiotensin (Ang II, 2 μg/kg/min) or norepinephrine (NE, 4 μg/kg/min). Thus, we will evaluate the therapeutic effect of AAV/SM22-BKα or AAV/MusB-BKα gene delivery in mice with two forms of hypertension. The blood pressure profile of our Ang II-infused C57BL/6J mice includes a resting mean arterial pressure of 110 mm Hg, which rapidly rises over one week and is maintained at 150 to 160 mm Hg by Ang II infusion (FIG. 9A). The osmotic minipumps last up to six weeks, but a second pump can be inserted to maintain the hypertension and permit evaluation of long-term antihypertensive therapies (FIG. 9B, arrow, top trace). The increase in blood pressure is reversible, and returns to normal if the Ang II pump is replaced with a saline pump (FIG. 9B, arrow, lower trace). Similar levels of chronic hypertension can be established by infusing 4 μg/kg/min NE (FIG. 9C).

Example 6

AAV/SM22-BKα Reverses Ang II-induced Hypertension

In the typical clinical situation a patient's blood pressure is elevated at diagnosis, and the therapeutic value of an antihypertensive treatment relies on its ability to normalize the elevated pressure without unwanted side effects. To explore this question, mice were instrumented with telemetry transmitters for two weeks to obtain baseline blood pressure recordings. Subsequently, Ang II-minipumps were implanted to induce hypertension. At 7 and 10 days after the start of Ang II infusion when blood pressure was elevated (mean arterial pressure ~140 mm Hg), AAV/SM22-GFP or AAV/SM22-BKα were injected (2 tail vein injections; $5 \times 10^{10}$ vp/kg; 3 days apart) into two mice each. Mean arterial pressure was monitored for 6 weeks following the virus injection, with telemetry lost in one mouse injected with AAV/SM22-BKα. However, all mice in the study appeared healthy and showed similar weights for the full 6 weeks of the study. As expected, Ang II infusion established chronic hypertension in mice injected with AAV/SM22-GFP for 6 weeks (FIG. 11, top trace). In contrast, blood pressure fell continuously for 7 days in the mouse injected with AAV/SM22-BKα, and remained low for 5 weeks. The moderate rebound in blood pressure during the 2nd and 3rd weeks after AAV injection seems to correlate with the bimodal expression of AAV-transduced genes that have been observed to show a transient expression peak at 1 to 2 weeks, followed by an abating period that precedes strong continuous gene expression.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

What is claimed is:

1. A method of treating hypertension by expressing a calcium-activated potassium channel in a smooth muscle cell, the method comprising contacting the smooth muscle cell of a subject having hypertension with an adeno-associated viral (AAV) vector comprising a smooth muscle specific promoter that is SEQ ID NO: 2 or 3, the smooth muscle specific promoter operably-linked to a nucleic acid sequence encoding a calcium-activated potassium channel.

2. The method of claim 1, wherein the nucleic acid sequence encoding a calcium-activated potassium channel encodes a BKα subunit.

3. The method of claim 1, wherein the nucleic acid sequence encoding a calcium-activated potassium channel is SEQ ID NO: 4, SEQ ID NO: 6, SEQ ID NO: 7, or SEQ ID NO: 8.

4. A method for treating hypertension by administering an adeno-associated viral (AAV) vector encoding a calcium-activated potassium channel operatively linked to an SM22α promoter that is SEQ ID NO: 2 or 3 into vascular smooth muscle cells of a subject having hypertension, thereby decreasing blood pressure of the subject and expressing a calcium-activated potassium channel in a smooth muscle cell.

* * * * *

SEQUENCE LISTING

<160> NUMBER OF SEQ ID NOS: 11

<210> SEQ ID NO 1
<211> LENGTH: 507
<212> TYPE: DNA
<213> ORGANISM: Mus musculus

<400> SEQUENCE: 1

```
ctgcagtcaa gactagttcc caccaactcg attttaaagc cttgcaagaa ggtggcttgt      60
ttgtcccttg caggttcctt tgtcgggcca aactctagaa tgcctccccc tttctttctc     120
attgaagagc agacccaagt ccgggtaaca aggaagggtt tcagggtcct gcccataaaa     180
ggttttccc ggccgccctc agcaccgccc gccccgacc cccgcagcat ctccaaagca      240
tgcagagaat gtctccggct gccccgaca gactgctcca acttggtgtc tttccccaaa     300
tatggagcct gtgtggagtg agtggggcgg cccggggtgg tgagccaagc agacttccat     360
gggcagggag gggcgccagc ggacggcaga ggggtgacat cactgcctag gcggccttta     420
aaccctcac ccagccggcg ccccagcccg tctgccccag cccagacacc gaagctactc      480
tccttccagt ccacaaacga ccaagcc                                         507
```

<210> SEQ ID NO 2
<211> LENGTH: 499
<212> TYPE: DNA
<213> ORGANISM: Mus musculus

<400> SEQUENCE: 2

```
ctgcagtcaa gactagttcc caccaactcg attttaaagc cttgcaagaa ggtggcttgt      60
ttgtcccttg caggttcctt tgtcgggcca aactctagaa tgcctccccc tttctttctc     120
attgaagagc agacccaagt ccgggtaaca aggaagggtt tcagggtcct gcccataaaa     180
ggttttccc tcagcaccgc cccgccccga ccccgcagc atctccaaag catgcagaga       240
atgtctccgg ctgccccga cagactgctc aacttggtg tctttcccca aatatggagc      300
ctgtgtggag tgagtggggc ggcccggggt ggtgagccaa gcagacttcc atgggcaggg     360
aggggcgcca gcggacggca gagggtgac atcactgcct aggcggcctt taaaccctc      420
acccagccgg cgccccagcc cgtctgcccc agcccagaca ccgaagctac tctccttcca     480
gtccacaaac gaccaagcc                                                  499
```

<210> SEQ ID NO 3
<211> LENGTH: 246
<212> TYPE: DNA
<213> ORGANISM: Mus musculus

<400> SEQUENCE: 3

```
atcaaaggag gaggagccag gaggggagag aggtgggagg gagggtcctc cggaaggact      60
ccaaatttag acagagggtg ggggaaacgg gatataaagg aactggagct tgaggacag      120
atagagagac tctgcggccc aggtaagagg aggtttgggg tgggatgccc tgcagcccgt     180
ccacagagcc cccaccgtga gggacctcct tcaccaggag tggggtgcag gtcagttgga     240
ggccta                                                                246
```

<210> SEQ ID NO 4
<211> LENGTH: 3555
<212> TYPE: DNA
<213> ORGANISM: Mus musculus

```
<400> SEQUENCE: 4
atgagcagca atatccacgc gaacaatctc agcctagacg cgtcctcctc ctcctcttcc      60
tcctcctctt cttcttcttc ctcctcctct tcctcctcgt cctcggtcca cgagcccaag     120
atggatgcgc tcatcatacc ggtgaccatg gaggtgccgt gcgacagccg gggccaacgc     180
atgtggtggg ctttcttggc ctcctccatg gtgactttct tcggggggcct cttcatcatc    240
ttgctctggg ggacgctcaa gtacctgtgg accgtttgct gccactgcgg gggcaagacg     300
aaggaggccc agaagataaa caatggctcc agccaggcag atggtactct caagccagtg     360
gacgaaaaag aggaggtggt ggcagccgag gtcggctgga tgacatctgt gaaggactgg     420
gcaggggtga tgatatccgc ccagacactg actggcagag tcctggttgt gttagtcttt     480
gctctcagca ttggtgccct cgtaatatac ttcatagact cgtcaaaccc aatagaatcc     540
tgccagaatt tctacaaaga tttcacatta cagatcgaca tggcttttca cgtgttcttc     600
ctcctctact ttggcttgcg gtttattgca gccaacgata agctgtggtt ctggctggaa     660
gtgaattcag tagtagattt cttcacagtc cctcctgtgt ttgtgtctgt gtacttaaac     720
agaagttggc ttggcttgag attttttaaga gctctcagac tgatacagtt ttcagagatt     780
ttgcagtttc tgaatatcct taaaacaagt aactccatca agctggtgaa tctgctctcc     840
atatttatca gcacgtggct gactgcagct ggattcatcc acttggtgga gaattcaggg     900
gacccatggg aaaatttcca aaacaaccag gcacttacgt actgggaatg tgtctactta     960
ctcatggtca aatgtctac agtgggttat ggggacgttt atgcaaaaac cacacttgga    1020
cgcctcttca tggtcttctt catcctcggg ggactggcca tgtttgccag ctacgtccct    1080
gaaatcatag agttaatagg aaaccgcaag aaatacgggg gctcctatag cgcggttagt    1140
ggaagaaagc acattgtagt ctgtggacac attactctgg agagtgtctc taacttcctg    1200
aaggactttc tgcacaagga ccgggatgat gtcaacgtgg agattgtctt tcttcacaac    1260
atctcccta accttgagct tgaagctctg ttcaaacggc atttcactca ggtggagttt    1320
tatcagggct ctgtcctcaa tccacatgat cttgccagag tcaagataga gtcagcagat    1380
gcatgcctga tccttgccaa taagtattgc gctgacccgg atgcagaaga tgcctccaac    1440
atcatgagag tgatctccat caaaaactac cacccaaaga tcaggatcat cactcagatg    1500
ctgcagtatc acaacaaggc ccatctgctc aacatcccca gctggaactg gaagagggt    1560
gatgacgcaa tatgccttgc agagctcaag ttgggtttca tagcccagag ctgtctggct    1620
caaggcctct ccacaatgct tgccaatctc ttctctatga ggtcattcat aaagattgag    1680
gaagacacat ggcagaaata ctacttggaa ggagtctcca atgaaatgta cacagaatat    1740
ctctccagtg ccttcgtggg tctgtccttc cctactgttt gtgagctgtg ttttgtgaag    1800
cttaagctcc tgatgatagc cattgagtac aagtctgcca acagagagag ccgaagccga    1860
aagcgaatat taattaaccc tgggaaccac cttaagatcc aagaaggtac tttaggattt    1920
ttcatcgcaa gtgatgccaa agaagttaaa agggcatttt tttactgcaa ggcctgtcat    1980
gatgacgtca cagatcccaa aagaattaaa aaatgtggct gcaggcggct tgaagatgag    2040
cagccgccaa ccctgtcacc aaaaaaaaaa caacgtaatg ggggcatgag gaactcgccc    2100
aacacctccc cgaagctgat gaggcatgac cccttgttaa ttcctggcaa tgatcagatt    2160
gacaacatgg actccaatgt gaaaaagtac gactccactg gaatgtttca ctggtgtgca    2220
cccaaggaga ttgagaaagt catcttgact cgaagtgaag ctgccatgac tgtcctgagt    2280
ggccatgtcg tagtctgcat cttttgggggat gtcagctcag cccrgattgg cctccggaac    2340
```

| | |
|---|---|
| ctggtgatgc cacttcgtgc tagcaacttt cactatcatg agcrcaaaca cattgtgttt | 2400 |
| gtgggctcca ttgagtacct caagagggag tgggaaacac tgcacaactt cccgaaagtg | 2460 |
| tccatattgc ctggtacacc attaagtcgg gctgatttaa gggctgtcaa catcaacctc | 2520 |
| tgtgacatgt gcgttatcct gtcagccaat cagaataata ttgatgatac ttcgcttcag | 2580 |
| gacaaggaat gcatcttggc gtcactcaac atcaaatcta tgcagtttga tgacagcatc | 2640 |
| ggggtcttgc aggctaattc ccaaggattc acacctcctg gaatggacag atcatcaccc | 2700 |
| gacaacagcc cagtgcacgg gatgttacgc cagccgtcca tcacaactgg ggtcaacatt | 2760 |
| cccatcatca cggaactcgc taagccgggc aagttgcctt tggtatcagt caatcaggaa | 2820 |
| aaaaacagtg ggacgcacat tctaatgata acggagttgg tgaatgatac caatgttcag | 2880 |
| tttttggacc aagacgatga cgatgaccct gacacagagc tgtacctcac acagcccttt | 2940 |
| gcttgtggga cagcatttgc cgtcagcgtc ctggactcac tcatgagcgc gacatacttc | 3000 |
| aatgacaata tcctcaccct aatacggacc ctggtgacag gaggagccac accagagctc | 3060 |
| gaggctctaa tagctgagga gaatgcactt cgaggaggct acagcactcc gcagacattg | 3120 |
| gccaacaggg accgttgccg agtggcccag ttagccctgt tagatggtcc ctttgcagac | 3180 |
| ttaggggatg gtggttgtta tggtgatctg ttctgcaaag ctctgaaaac atataatatg | 3240 |
| ctttgttttg gaatttaccg gctgagagat gcccacctca gcaccccag ccagtgtaca | 3300 |
| aaaaggtacg tcatcaccaa tcctccctac gagtttgagc tcgtaccaac agacctgatc | 3360 |
| ttctgcctga tgcagtttga ccacaacgct ggccaatccc gggccagtct gtctcattcc | 3420 |
| tcccactcct cacagtcgtc cagtaagaag agctcctccg tccactccat cccgtccaca | 3480 |
| gcaaatcggc cgaaccggcc caagtccagg gagtcccgcg acaaacagaa cagaaaagaa | 3540 |
| atggtttaca gatga | 3555 |

<210> SEQ ID NO 5
<211> LENGTH: 9188
<212> TYPE: DNA
<213> ORGANISM: Artificial Sequence
<220> FEATURE:
<223> OTHER INFORMATION: BASED ON MUS MUSCULUS

<400> SEQUENCE: 5

| | |
|---|---|
| cgtatcacga ggccctttcg tcttcaagaa ttctcatgtt tgacagctta tcatcgataa | 60 |
| gctttaatgc ggtagtttat cacagttaaa ttgctaacgc agtcaggcac cgtgtatgaa | 120 |
| atctaacaat gcgctcatcg tcatcctcgg caccgtcacc ctggatgctg taggcatagg | 180 |
| cttggttatg ccggtactgc cgggcctctt gcgggatatc gtccattccg acagcatcgc | 240 |
| cagtcactat ggcgtgctgc tagcgctata tgcgttgatg caatttctat gcgcacccgt | 300 |
| tctcggagca ctgtccgacc gctttggccg ccgcccagtc ctgctcgctt cgctacttgg | 360 |
| agccactatc gactacgcga tcatggcgac cacacccgtc ctgtggatcc tctacgccgg | 420 |
| acgcatcgtg gccggcatca ccggcgccac aggtgcggtt gctggcgcct atatcgccga | 480 |
| catcaccgat ggggaagatc gggctcgcca cttcggcctc atgagcgctt gtttcggcgt | 540 |
| gggtatggtg gcaggccccg tggccggggg actgttgggc gccatctcct tgcatgcacc | 600 |
| attccttgcg gcggcggtgc tcaacggcct caacctacta ctgggctgct tcctaatgca | 660 |
| ggagtcgcat aagggagagc gtcgaccgat gcccttgaga gccttcaacc cagtcagctc | 720 |
| cttccggtgg gcgcggggca tgactatcgt cgccgcactt atgactgtct tctttatcat | 780 |
| gcaactcgta ggacaggtgc cggcagcgct ctgggtcatt ttcggcgagg accgctttcg | 840 |

-continued

```
ctggagcgcg acgatgatcg gcctgtcgct tgcggtattc ggaatcttgc acgccctcgc    900
tcaagccttc gtcactggtc ccgccaccaa acgtttcggc gagaagcagg ccattatcgc    960
cggcatggcg gccgacgcgc tgggctacgt cttgctggcg ttcgcgacgc gaggctggat   1020
ggccttcccc attatgattc ttctcgcttc cggcggcatc gggatgcccg cgttgcaggc   1080
catgctgtcc aggcaggtag atgacgacca tcagggacag cttcaaggat cgctcgcggc   1140
tcttaccagc ctaacttcga tcactggacc gctgatcgtc acggcgattt atgccgcctc   1200
ggcgagcaca tggaacgggt tggcatggat tgtaggcgcc gccctatacc ttgtctgcct   1260
ccccgcgttg cgtcgcggtg catggagccg gccacctcg acctgaatgg aagccggcgg    1320
cacctcgcta acggattcac cactccaaga attggagcca atcaattctt gcggagaact   1380
gtgaatgcgc aaaccaaccc ttggcagaac atatccatcg cgtccgccat ctccagcagc   1440
cgcacgcggc gcatctcggg cagcgttggg tcctggccac gggtgcgcat gatcgtgctc   1500
ctgtcgttga ggacccggct aggctggcgg ggttgcctta ctggttagca gaatgaatca   1560
ccgatacgcg agcgaacgtg aagcgactgc tgctgcaaaa cgtctgcgac ctgagcaaca   1620
acatgaatgg tcttcggttt ccgtgtttcg taaagtctgg aaacgcggaa gtcagcgccc   1680
tgcaccatta tgttccggat ctgcatcgca ggatgctgct ggctaccctg tggaacacct   1740
acatctgtat taacgaagcg ctggcattga ccctgagtga ttttctctg gtcccgccgc    1800
atccataccg ccagttgttt accctcacaa cgttccagta accgggcatg ttcatcatca   1860
gtaacccgta tcgtgagcat cctctctcgt ttcatcggta tcattacccc catgaacaga   1920
aatccccctt acacggaggc atcagtgacc aaacaggaaa aaaccgccct taacatggcc   1980
cgctttatca gaagccagac attaacgctt ctggagaaac tcaacgagct ggacgcggat   2040
gaacaggcag acatctgtga atcgcttcac gaccacgctg atgagcttta ccgcagctgc   2100
ctcgcgcgtt tcggtgatga cggtgaaaac ctctgacaca tgcagctccc ggagacggtc   2160
acagcttgtc tgtaagcgga tgccgggagc agacaagccc gtcagggcgc gtcagcgggt   2220
gttggcgggt gtcggggcgc agccatgacc cagtcacgta gcgatagcgg agtgtatact   2280
ggcttaacta tgcggcatca gagcagattg tactgagagt gcaccatatg cggtgtgaaa   2340
taccgcacag atgcgtaagg agaaaatacc gcatcaggcg ctcttccgct tcctcgctca   2400
ctgactcgct gcgctcggtc gttcggctgc ggcgagcggt atcagctcac tcaaaggcgg   2460
taatacggtt atccacagaa tcaggggata acgcaggaaa gaacatgtga gcaaaaggcc   2520
agcaaaaggc caggaaccgt aaaaaggccg cgttgctggc gttttccat aggctccgcc    2580
cccctgacga gcatcacaaa aatcgacgct caagtcagag gtggcgaaac ccgacaggac   2640
tataaagata ccaggcgttt ccccctggaa gctccctcgt gcgctctcct gttccgaccc   2700
tgccgcttac cggatacctg tccgcctttc tcccttcggg aagcgtggcg ctttctcata   2760
gctcacgctg taggtatctc agttcggtgt aggtcgttcg ctccaagctg ggctgtgtgc   2820
acgaaccccc cgttcagccc gaccgctgcg ccttatccgg taactatcgt cttgagtcca   2880
acccggtaag acacgactta tcgccactgg cagcagccac tggtaacagg attagcagag   2940
cgaggtatgt aggcggtgct acagagttct tgaagtggtg gcctaactac ggctacacta   3000
gaaggacagt atttggtatc tgcgctctgc tgaagccagt taccttcgga aaaagagttg   3060
gtagctcttg atccggcaaa caaaccaccg ctggtagcgg tggttttttt gtttgcaagc   3120
agcagattac gcgcagaaaa aaaggatctc aagaagatcc tttgatcttt tctacggggt   3180
ctgacgctca gtggaacgaa aactcacgtt aagggatttt ggtcatgaga ttatcaaaaa   3240
```

```
ggatcttcac ctagatcctt ttaaattaaa aatgaagttt taaatcaatc taaagtatat   3300
atgagtaaac ttggtctgac agttaccaat gcttaatcag tgaggcacct atctcagcga   3360
tctgtctatt tcgttcatcc atagttgcct gactccccgt cgtgtagata actacgatac   3420
gggagggctt accatctggc cccagtgctg caatgatacc gcgagaccca cgctcaccgg   3480
ctccagattt atcagcaata accagccag ccggaagggc cgagcgcaga agtggtcctg    3540
caactttatc cgcctccatc cagtctatta attgttgccg ggaagctaga gtaagtagtt   3600
cgccagttaa tagtttgcgc aacgttgttg ccattgctgc agggggggg ggccccttg     3660
gccactccct ctctgcgcgc tcgctcgctc actgaggccg ggcgaccaaa ggtcgcccga   3720
cgcccgggct tgcccgggc ggcctcagtg agcgagcgag cgcgcagaga gggagtggcc    3780
aactccatca ctaggggttc cagatcctcg agctgcagtc aagactagtt cccaccaact   3840
cgattttaaa gccttgcaag aaggtggctt gtttgtccct tgcaggttcc tttgtcgggc   3900
caaactctag aatgcctccc cctttctttc tcattgaaga gcagacccaa gtccgggtaa   3960
caaggaaggg tttcagggtc ctgcccataa aaggtttttc ccggccgccc tcagcaccgc   4020
cccgccccga ccccgcagc atctccaaag catgcagaga atgtctccgg ctgccccga    4080
cagactgctc caacttggtg tctttcccca aatatggagc ctgtgtggag tgagtggggc   4140
ggcccggggt ggtgagccaa gcagacttcc atgggcaggg aggggcgcca gcggacggca   4200
gaggggtgac atcactgcct aggcggcctt taaacccctc acccagccgg cgccccagcc   4260
cgtctgcccc agcccagaca ccgaagctac tctccttcca gtccacaaac gaccaagcca   4320
gatctggtac catgagcagc aatatccacg cgaacaatct cagcctagac gcgtcctcct   4380
cctcctcttc ctcctcctct tcttcttctt cctcctcctc ttcctcctcg tcctcggtcc   4440
acgagcccaa gatggatgcg ctcatcatac cggtgaccat ggaggtgccg tgcgacagcc   4500
ggggccaacg catgtggtgg gctttcttgg cctcctccat ggtgactttc ttcggggggcc   4560
tcttcatcat cttgctctgg cggacgctca agtacctgtg gaccgtttgc tgccactgcg   4620
ggggcaagac gaaggaggcc cagaagataa acaatggctc cagccaggca gatggtactc   4680
tcaagccagt ggacgaaaaa gaggaggtgg tggcagccga ggtcggctgg atgacatctg   4740
tgaaggactg gcagggggtg atgatatccg cccagacact gactggcaga gtcctggttg   4800
tgttagtctt tgctctcagc attggtgccc tcgtaatata cttcatagac tcgtcaaacc   4860
caatagaatc ctgccagaat ttctacaaag atttcacatt acagatcgac atggctttca   4920
acgtgttctt cctcctctac tttggcttgc ggtttattgc agccaacgat aagctgtggt   4980
tctggctgga agtgaattca gtagtagatt tcttcacagt ccctcctgtg tttgtgtctg   5040
tgtacttaaa cagaagttgg cttggcttga gatttttaag agctctcaga ctgatacagt   5100
tttcagagat tttgcagttt ctgaatatcc ttaaaacaag taactccatc aagctggtga   5160
atctgctctc catatttatc agcacgtggc tgactgcagc tggattcatc cacttggtgg   5220
agaattcagg ggacccatgg gaaaatttcc aaaacaacca ggcacttacg tactgggaat   5280
gtgtctactt actcatggtc acaatgtcta cagrgggtta tggggacgtt tatgcaaaaa   5340
ccacacttgg acgcctcttc atggtcttct tcarcctcgg gggactggcc atgtttgcca   5400
gctacgtccc tgaaatcata gagttaatag gaaaccgcaa gaaatacggg ggctcctata   5460
gcgcggttag tggaagaaag cacattgtag tctgtggaca cattactctg gagagtgtct   5520
ctaacttcct gaaggacttt ctgcacaagg accgggatga tgtcaacgtg gagattgtct   5580
ttcttcacaa catctcccct aaccttgagc ttgaagctct gttcaaacgg catttcactc   5640
```

-continued

```
aggtggagtt ttatcagggc tctgtcctca atccacatga tcttgccaga gtcaagatag   5700
agtcagcaga tgcatgcctg atccttgcca ataagtattg cgctgacccg gatgcagaag   5760
atgcctccaa catcatgaga gtgatctcca tcaaaaacta ccacccaaag atcaggatca   5820
tcactcagat gctgcagtat cacaacaagg cccatctgct caacatcccc agctggaact   5880
ggaaagaggg tgatgacgca atatgccttg cagagctcaa gttgggtttc atagcccaga   5940
gctgtctggc tcaaggcctc tccacaatgc ttgccaatct cttctctatg aggtcattca   6000
taaagattga ggaagacaca tggcagaaat actacttgga aggagtctcc aatgaaatgt   6060
acacagaata tctctccagt gccttcgtgg gtctgtcctt ccctactgtt tgtgagctgt   6120
gttttgtgaa gcttaagctc ctgatgatag ccattgagta caagtctgcc aacagagaga   6180
gccgaagccg aaagcgaata ttaattaacc ctgggaacca ccttaagatc caagaaggta   6240
ctttaggatt tttcatcgca agtgatgcca agaagttaa aagggcattt ttttactgca   6300
aggcctgtca tgatgacgtc acagatccca aaagaattaa aaaatgtggc tgcaggcggc   6360
ttgaagatga gcagccgcca accctgtcac caaaaaaaaa acaacgtaat gggggcatga   6420
ggaactcgcc caacacctcc ccgaagctga tgaggcatga ccccttgtta attcctggca   6480
atgatcagat tgacaacatg gactccaatg tgaaaaagta cgactccact ggaatgtttc   6540
actggtgtgc acccaaggag attgagaaag tcatcttgac tcgaagtgaa gctgccatga   6600
ctgtcctgag tggccatgtc gtagtctgca tctttgggga tgtcagctca gccctgattg   6660
gcctccggaa cctggtgatg ccacttcgtg ctagcaactt tcactatcat gagctcaaac   6720
acattgtgtt tgtgggctcc attgagtacc tcaagaggga gtgggaaaca ctgcacaact   6780
tcccgaaagt gtccatattg cctggtacac cattaagtcg ggctgattta agggctgtca   6840
acatcaacct ctgtgacatg tgcgttatcc tgtcagccaa tcagaataat attgatgata   6900
cttcgcttca ggacaaggaa tgcatcttgg cgtcactcaa catcaaatct atgcagtttg   6960
atgacagcat cggggtcttg caggctaatt cccaaggatt cacacctcct ggaatggaca   7020
gatcatcacc cgacaacagc ccagtgcacg ggatgttacg ccagccgtcc atcacaactg   7080
gggtcaacat tccatcatc acggaactcg ctaagccggg caagttgcct ttggtatcag   7140
tcaatcagga aaaaacagt gggacgcaca ttctaatgat aacggagttg gtgaatgata   7200
ccaatgttca gttttggac caagacgatg acgatgaccc tgacacagag ctgtacctca   7260
cacagcccct tgcttgtggg acagcatttg ccgtcagcgt cctggactca ctcatgagcg   7320
cgacatactt caatgacaat atcctcaccc taatacggac cctggtgaca ggaggagcca   7380
caccagagct cgaggctcta atagctgagg agaatgcact tcgaggaggc tacagcactc   7440
cgcagacatt ggccaacagg gaccgttgcc gagtggccca gttagccctg ttagatggtc   7500
cctttgcaga cttaggggat ggtggttgtt atggtgatct gttctgcaaa gctctgaaaa   7560
catataatat gctttgtttt ggaatttacc ggctgagaga tgcccacctc agcacccca   7620
gccagtgtac aaaaaggtac gtcatcacca atcctcccta cgagtttgag ctcgtaccaa   7680
cagacctgat cttctgcctg atgcagtttg accacaacgc tggccaatcc cgggccagtc   7740
tgtctcattc ctcccactcc tcacagtcgt ccagtaagaa gagctcctcc gtccactcca   7800
tcccgtccac agcaaatcgg ccgaaccggc ccaagtccag ggagtcccgc gacaaacaga   7860
acagaaaaga aatggtttac agatgatcta gagtcggggc ggccggccgc ttcgagcaga   7920
catgataaga tacattgatg agtttggaca accacaact agaatgcagt gaaaaaatg   7980
ctttatttgt gaaatttgtg atgctattgc tttatttgta accattataa gctgcaataa   8040
```

```
acaagttaac aacaacaatt gcattcattt tatgtttcag gttcagggg  aggtgtggga      8100
ggttttttaa agcaagtaaa acctctacaa atgtggtaaa atcgataagg atctactcgt      8160
aatctgtaat tgcttgttaa tcaataaacc gtttaattcg tttcagttga actttggtct      8220
ctgcgtattt ctttcttatc tagttttcat ggctacgtag ataagtagca tggcgggtta      8280
atcattaact acaaggaacc cctagtgatg gagttggcca ctccctctct gcgcgctcgc      8340
tcgctcactg aggccgggcg accaaaggtc gcccgacgcc cgggctttgc ccgggcggcc      8400
tcagtgagcg agcgagcgcg cagagaggga gtggccaagg gggggggggg ggggggggcc      8460
cccctgcagg catcgtggtg tcacgctcgt cgtttggtat ggcttcattc agctccggtt      8520
cccaacgatc aaggcgagtt acatgatccc ccatgttgtg caaaaaagcg gttagctcct      8580
tcggtcctcc gatcgttgtc agaagtaagt tggccgcagt gttatcactc atggttatgg      8640
cagcactgca taattctctt actgtcatgc catccgtaag atgctttct  gtgactggtg      8700
agtactcaac caagtcattc tgagaatagt gtatgcggcg accgagttgc tcttgcccgg      8760
cgtcaacacg ggataatacc gcgccacata gcagaacttt aaaagtgctc atcattggaa      8820
aacgttcttc ggggcgaaaa ctctcaagga tcttaccgct gttgagatcc agttcgatgt      8880
aacccactcg tgcacccaac tgatcttcag catcttttac tttcaccagc gtttctgggt      8940
gagcaaaaac aggaaggcaa aatgccgcaa aaaagggaat aagggcgaca cggaaatgtt      9000
gaatactcat actcttcctt tttcaatatt attgaagcat ttatcagggt tattgtctca      9060
tgagcggata catatttgaa tgtatttaga aaaataaaca aataggggtt ccgcgcacat      9120
ttccccgaaa agtgccacct gacgtctaag aaaccattat tatcatgaca ttaacctata      9180
aaaatagg                                                              9188

<210> SEQ ID NO 6
<211> LENGTH: 6103
<212> TYPE: DNA
<213> ORGANISM: Homo sapiens

<400> SEQUENCE: 6
cgccaggtcg cgcacagcgc cccgagccca ggcgcctccc cgccccctc  ccgcgctccg        60
cggcggcggc ggcggcggca gcagtagcag caatatggct gttgatgggt gtttggggtg       120
gcgctggcgg cgggaggagc tcccccgagc ccctgcgccg gctgcccgtt gctagctatg       180
gcaaatggtg gcggcggcgg cggcggcagc agcggcggcg gcggcggcgg cggaggcagc       240
agtcttagaa tgagtagcaa tatccacgcg aaccatctca gcctagacgc gtcctcctcc       300
tcctcctcct cctcttcctc ttcttcttct tcctcctcct cttcctcctc gtcctcggtc       360
cacgagccca agatggatgc gctcatcatc ccggtgacca tggaggtgcc gtgcgacagc       420
cggggccaac gcatgtggtg ggcttttcctg gcctcctcca tggtgacttt cttcggggc        480
ctcttcatca tcttgctctg gcggacgctc aagtacctgt ggaccgtgtg ctgccactgc       540
gggggcaaga cgaaggaggc ccagaagatt aacaatggct caagccaggc ggatggcact       600
ctcaaaccag tggatgaaaa agaggaggca gtggccgccg aggtcggctg gatgacctcc       660
gtgaaggact gggcggggt  gatgatatcc gcccagacac tgactggcag agtcctggtt       720
gtcttagtct ttgctctcag catcggtgca cttgtaatat acttcataga ttcatcaaac       780
ccaatagaat cctgccagaa tttctacaaa gatttcacat tacagatcga catggctttc       840
aacgtgttct tccttctcta cttcggcttg cggtttattg cagccaacga taaattgtgg       900
ttctggctgg aagtgaactc tgtagtggat ttcttcacgg tgccccccgt gtttgtgtct       960
```

```
gtgtacttaa acagaagttg gcttggtttg agatttttaa gagctctgag actgatacag    1020
ttttcagaaa ttttgcagtt tctgaatatt cttaaaacaa gtaattccat caagctggtg    1080
aatctgctct ccatatttat cagcacgtgg ctgactgcag ccgggttcat ccatttggtg    1140
gagaattcag gggacccatg ggaaaatttc caaaacaacc aggctctcac ctactgggaa    1200
tgtgtctatt tactcatggt cacaatgtcc accgttggtt atggggatgt ttatgcaaaa    1260
accacacttg ggcgcctctt catggtcttc ttcatcctcg gggactggc catgtttgcc     1320 agctacgtcc ctgaaatcat agagttaata ggaaaccgca agaaatacgg gggctcctat    1380
agtgcggtta gtgaagaaa gcacattgtg gtctgcggac acatcactct ggagagtgtt     1440
tccaacttcc tgaaggactt tctgcacaag gaccgggatg acgtcaatgt ggagatcgtt    1500
tttcttcaca acatctcccc caacctggag cttgaagctc tgttcaaacg acattttact    1560
caggtggaat tttatcaggg ttccgtcctc aatccacatg atcttgcaag agtcaagata    1620
gagtcagcag atgcatgcct gatccttgcc aacaagtact cgcgctgaccc ggatgcggag   1680 gatgcctcga atatcatgag agtaatctcc ataaagaact accatccgaa gataagaatc    1740
atcactcaaa tgctgcagta tcacaacaag gcccatctgc taaacatccc gagctggaat    1800 tggaagaag gtgatgacgc aatctgcctc gcagagttga agttgggctt catagcccag     1860
agctgcctgg ctcaaggcct ctccaccatg cttgccaacc tcttctccat gaggtcattc    1920
ataaagattg aggaagacac atggcagaaa tactacttgg aaggagtctc aaatgaaatg    1980
tacacagaat atctctccag tgccttcgtg ggtctgtcct ccctactgt ttgtgagctg      2040 tgttttgtga agctcaagct cctaatgata gccattgagt acaagtctgc caaccgagag    2100
agccgtatat taattaatcc tggaaaccat cttaagatcc aagaaggtac tttaggattt    2160
ttcatcgcaa gtgatgccaa agaagttaaa agggcatttt tttactgcaa ggcctgtcat    2220
gatgacatca cagatcccaa aagaataaaa aaatgtggct gcaaacggct tgaagatgag    2280
cagccgtcaa cactatcacc aaaaaaaag caacggaatg gaggcatgcg gaactcaccc     2340
aacacctcgc ctaagctgat gaggcatgac cccttgttaa ttcctggcaa tgatcagatt    2400
gacaacatgg actccaatgt gaagaagtac gactctactg ggatgttca ctggtgtgca     2460 cccaaggaga tagagaaagt catcctgact cgaagtgaag ctgccatgac cgtcctgagt    2520
ggccatgtcg tggtctgcat cttttggcgac gtcagctcag ccctgatcgg cctccggaac   2580
ctggtgatgc cgctccgtgc cagcaacttt cattaccatg agctcaagca cattgtgttt    2640
gtgggctcta ttgagtacct caagcgggaa tgggagacgc ttcataactt ccccaaagtg    2700
tccatattgc ctggtacgcc attaagtcgg gctgatttaa gggctgtcaa catcaacctc    2760
tgtgacatgt gcgttatcct gtcagccaat cagaataata ttgatgatac ttcgctgcag    2820
gacaaggaat gcatcttggc gtcactcaac atcaaatcta tgcagtttga tgacagcatc    2880
ggagtcttgc aggctaattc ccaagggttc acacctccag gaatggatag atcctctcca    2940
gataacagcc cagtgcacgg gatgttacgt caaccatcca tcacaactgg ggtcaacatc    3000
cccatcatca ctgaactagt gaacgatact aatgttcagt ttttggacca agacgatgat    3060
gatgaccctg atacagaact gtacctcacg cagcccttg cctgtgggac agcatttgcc     3120
gtcagtgtcc tggactcact catgagcgcg acgtacttca tgacaatat cctcaccctg     3180 atacggaccc tggtgaccgg aggagccacg ccggagctgg aggctctgat tgctgaggaa    3240
aacgccctta gaggtggcta cagcaccccg cagacactgg ccaatagga ccgctgccgc      3300 gtggcccagt tagctctgct cgatgggcca tttgcggact taggggatgg tggttgttat    3360
```

```
ggtgatctgt tctgcaaagc tctgaaaaca tataatatgc tttgttttgg aatttaccgg    3420
ctgagagatg ctcacctcag cacccccagt cagtgcacaa agaggtatgt catcaccaac    3480
ccgccctatg agtttgagct cgtgccgacg gacctgatct tctgcttaat gcagtttgac    3540
cacaatgccg gccagtcccg ggccagcctg tcccattcct cccactcgtc gcagtcctcc    3600
agcaagaaga gctcctctgt tcactccatc ccatccacag caaaccgaca gaaccggccc    3660
aagtccaggg agtcccggga caaacagaag tacgtgcagg aagagcggct ttgatatgtg    3720
tatccaccgc cactgtgtga aactgtatct gccactcatt tccccagttg gtgtttccaa    3780
caaagtaact ttccctgttt tcccctgtag tccccccctt ttttttttaca catatttgca    3840
tatgtatgat agtgtgcatg tggttgtcat ttttatttca ccaccataaa acccttgagc    3900
acaacagcaa ataagcagac ggaccaaaag ttatttatga ttctggggga aaaataaccc    3960
aaaggcatgc tccagacata aatagctcac tgcaggaacg agttcacaga ttagaaggga    4020
gcacttgtga tcaacgtcag ttaggcagag caagtttatt taatgtaaaa gaaaagttga    4080
ttctgattta tcaggattat cagggtgctt tgggttttga ttttgttgtt gttgttgttt    4140
tcctttcttt ctttttttat acacacaata agttagcaca tgtttatttg aaacaagcaa    4200
ccaaacagca atgaaaacat attgattgtt tccagtctct gggccgaagt attgcgaagc    4260
atttgaaaag ctttcacgat ttgtgtagat gattatgaag acctgcttg ttgcaagaga     4320
acatcagtga ttttttttagt tactcaccaa ggccttttgt cccagagcca gttccctctg   4380
ggagttctta tgaacatttc tcaccttaat atggaggaga gaatagtatt ccaatcatgg    4440
atgtatcaaa ttctagtcat ttagtttaag tgaaagagg tttgattgca tattaaattg     4500
ttattctgtc tccttatgtt gccatatgaa tagctatttt ttttctttca cttttgacat    4560
ttgggatgaa aagccatatg tatcataaat atcagatgta agtcattaaa aactgccttc    4620
ctgggacttt tacatctttt aaaaggtgaa ttacttacct tatgtacaga ataaataatg    4680
ctcaggaaag agcaagtatt tttccatgca ttctcagggg atcttttac tcccctttgt     4740
ttgattagtt agggccccaa tgccaggtag gaggaagggc tggggcaatg gtagagtgag    4800
aggaagacaa acccagctgc agatcatgct tttctaggag ccgacatgct aaataaatta    4860
gaatgtagga ggatcagcca cagttgactc aacaaagaca aaagccagcc accaccttca    4920
actgttggca cagctgtgcg gtgctggctg tcccaatgca gaaagctggt gggaaggaat    4980
tcctcatcat cactttcttt aatgtagcca atttaggcag ggtaatgacg gcaatagaga    5040
gctgctcctt gtcattatga gacgtgggat aagaagagtg caacagtgag ccaaacacat    5100
tttggtatag ttattttttt cttcttttgt tttctttctt ttttaacact tagtaagcat    5160
gagaggagag gtagaaaaat acccttttt caacatatag ttgtcagatg ctttgtgcat     5220
gcaaatcatg cttttaggcag tgcggtattt cttaaaaact ggccaattca ccataaccaa    5280
tttcccttat ggatggacta ggctggtata tacatatttg aaaagttta cttcaaagaa     5340
ttccatcgaa tagaataggg gtaaaaggga ggaggaaaac atgtcacagc tgtaccatct    5400
ctaaaaaggt gttttatgg tgaatgtttt ggatttagat tttggatccc ccgtcccctc     5460
aagcatgata gttttggata tttgcttgct gtgtgaattg acaagcactt ttactgacaa    5520
atggtgaggc tcagtcagaa cctccaccct cccccacacc aaagacaggg gcagcgtagt    5580
attcaaacca gtattgtggt ggggaataat tgtatacatg taaattatca agccctatga    5640
gtggaagaat tttttcaaat tattttttgtc cctctatata ttgatttata ttatgtataa   5700
ctatctcttt atataaacta tatataatta tatatatata actatataat tatatatata   5760
```

| | |
|---|---|
| taactatata tataactata tatatgtatc ccctagtatt ggatcatgaa gagctcttca | 5820 |
| tgcattcttt gcaaaggagg ttataaagtt acgccctcag aacatttata actataagaa | 5880 |
| tgtgccagtt aaagtgctca acaggaaata tgacagttta aaagcattgt aaaactcaca | 5940 |
| tagcttactt ctctctctaa agtgcaacaa ggatgaatag aatgggccaa ggtatgacaa | 6000 |
| ttaatggttc tgcatgacct agccactgct gggggttttc ttctataacg ttgtccttgt | 6060 |
| gaaaactttt gtgaaattaa aaaaaaagga gttacaaatt tta | 6103 |

<210> SEQ ID NO 7
<211> LENGTH: 11993
<212> TYPE: DNA
<213> ORGANISM: Homo sapiens

<400> SEQUENCE: 7

| | |
|---|---|
| cgccaggtcg cgcacagcgc cccgagccca ggcgcctccc cgccccctc ccgcgctccg | 60 |
| cggcggcggc ggcggcggca gcagtagcag caatatggct gttgatgggt gtttggggtg | 120 |
| gcgctggcgg cgggaggagc tccccgagc ccctgcgccg gctgcccgtt gctagctatg | 180 |
| gcaaatggtg gcgccggcgg cggcggcagc agcggcggcg gcggcggcgg cggaggcagc | 240 |
| agtcttagaa tgagtagcaa tatccacgcg aaccatctca gcctagacgc gtcctcctcc | 300 |
| tcctcctcct cctcttcctc ttcttcttct tcctcctcct cttcctcctc gtcctcggtc | 360 |
| cacgagccca agatggatgc gctcatcatc ccggtgacca tggaggtgcc gtgcgacagc | 420 |
| cggggccaac gcatgtggtg ggcttttcct gcctcctcca tggtgacttt cttcgggggc | 480 |
| ctcttcatca tcttgctctg gcggacgctc aagtacctgt ggaccgtgtg ctgccactgc | 540 |
| gggggcaaga cgaaggaggc ccagaagatt aacaatggct caagccaggc ggatggcact | 600 |
| ctcaaaccag tggatgaaaa agaggaggca gtggccgccg aggtcggctg gatgacctcc | 660 |
| gtgaaggact gggcggggt gatgatatcc gcccagacac tgactggcag agtcctggtt | 720 |
| gtcttagtct ttgctctcag catcggtgca cttgtaatat acttcataga ttcatcaaac | 780 |
| ccaatagaat cctgccagaa tttctacaaa gatttcacat tacagatcga catggcttc | 840 |
| aacgtgttct tccttctcta cttcggcttg cggtttattg cagccaacga taaattgtgg | 900 |
| ttctggctgg aagtgaactc tgtagtggat ttcrtcacgg tgccccccgt gtttgtgtct | 960 |
| gtgtacttaa acagaagttg gcttggtttg agatttttaa gagctctgag actgatacag | 1020 |
| ttttcagaaa ttttgcagtt tctgaatatt cttaaaacaa gtaattccat caagctggtg | 1080 |
| aatctgctct ccatatttat cagcacgtgg ctgactgcag ccgggttcat ccatttggtg | 1140 |
| gagaattcag gggacccatg gaaaatttc caaaacaacc aggctctcac ctactgggaa | 1200 |
| tgtgtctatt tactcatggt cacaatgtcc accgttggtt atgggatgt ttatgcaaaa | 1260 |
| accacacttg ggcgcctctt catggtcttc ttcatcctcg ggggactggc catgtttgcc | 1320 |
| agctacgtcc ctgaaatcat agagttaata ggaaaccgca gaaatacgg ggctccctat | 1380 |
| agtgcggtta gtggaagaaa gcacattgtg gtctgcggac acatcactct ggagagtgtt | 1440 |
| tccaacttcc tgaaggactt tctgcacaag gaccggatg acgtcaatgt ggagatcgtt | 1500 |
| tttcttcaca acatctcccc caacctggag cttgaagctc tgttcaaacg acatttact | 1560 |
| caggtggaat tttatcaggg ttccgtcctc aatccacatg atcttgcaag agtcaagata | 1620 |
| gagtcagcag atgcatgcct gatccttgcc aacaagtact gcgctgaccc ggatgcggag | 1680 |
| gatgcctcga atatcatgag agtaatctcc ataaagaact accatccgaa gataagaatc | 1740 |
| atcactcaaa tgctgcagta tcacaacaag gcccatctgc taaacatccc gagctggaat | 1800 |

```
tggaaagaag gtgatgacgc aatctgcctc gcagagttga agttgggctt catagcccag    1860
agctgcctgg ctcaaggcct ctccaccatg cttgccaacc tcttctccat gaggtcattc    1920
ataaagattg aggaagacac atggcagaaa tactacttgg aaggagtctc aaatgaaatg    1980
tacacagaat atctctccag tgccttcgtg ggtctgtcct tccctactgt tgtgagctg     2040 tgttttgtga agctcaagct cctaatgata gccattgagt acaagtctgc caaccgagag    2100
agccgaagcc gaaagcgtat attaattaat cctggaaacc atcttaagat ccaagaaggt    2160
actttaggat ttttcatcgc aagtgatgcc aaagaagtta aagggcatt ttttactgc      2220 aaggcctgtc atgatgacat cacagatccc aaaagaataa aaaatgtgg ctgcaaacgg     2280 cttgaagatg agcagccgtc aacactatca ccaaaaaaaa agcaacggaa tggaggcatg    2340
cggaactcac ccaacacctc gcctaagctg atgaggcatg accccttgtt aattcctggc    2400
aatgatcaga ttgacaacat ggactccaat gtgaagaagt acgactctac tgggatgttt    2460
cactggtgtg cacccaagga gatagagaaa gtcatcctga ctcgaagtga agctgccatg    2520
accgtcctga gtggccatgt cgtggtctgc atctttggcg acgtcagctc agccctgatc    2580
ggcctccgga acctggtgat gccgctccgt gccagcaact tcattacca tgagctcaag    2640 cacattgtgt tgtgggctc tattgagtac ctcaagcggg aatgggagac gcttcataac    2700
ttccccaaag tgtccatatt gcctggtacg ccattaagtc gggctgattt aagggctgtc    2760
aacatcaacc tctgtgacat gtgcgttatc ctgtcagcca atcagaataa tattgatgat    2820
acttcgctgc aggacaagga atgcatcttg gcgtcactca acatcaaatc tatgcagttt    2880
gatgacagca tcggagtctt gcaggctaat tcccaagggt tcacacctcc aggaatggat    2940
agatcctctc cagataacag cccagtgcac gggatgttac gtcaaccatc catcacaact    3000
ggggtcaaca tccccatcat cactgaacta gtgaacgata ctaatgttca gttttggac    3060 caagacgatg atgatgaccc tgatacagaa ctgtacctca cgcagccctt tgcctgtggg    3120
acagcatttg ccgtcagtgt cctggactca ctcatgagcg cgacgtactt caatgacaat    3180
atcctcaccc tgatacggac cctggtgacc ggaggagcca cgccggagct ggaggctctg    3240
attgctgagg aaaacgccct tagaggtggc tacagcaccc cgcagacact ggccaatagg    3300
gaccgctgcc gcgtggccca gttagctctg ctcgatgggc catttgcgga cttaggggat    3360
ggtggttgtt atggtgatct gttctgcaaa gctctgaaaa catataatat gctttgttt     3420 ggaatttacc ggctgagaga tgctcacctc agcaccccca gtcagtgcac aaagaggtat    3480
gtcatcacca acccgcccta tgagtttgag ctcgtgccga cggacctgat cttctgctta    3540 atgcagttg accacaatgc cggccagtcc cgggccagcc tgtcccattc ctcccactcg     3600
tcgcagtcct ccagcaagaa gagctcctct gttcactcca tcccatccac agcaaaccga    3660
cagaaccggc ccaagtccag ggagtcccgg gacaaacaga acagaaaaga aatggtttac    3720
agatgaaccg ataatgcct atcccagaaa cattcaaatc aagcccatga gtacccacat    3780
ggctaaccag atcaaccaat ataaatccac aagcagcttg attccaccaa tcagagaagt    3840
tgaagatgaa tgttgactcc caggagacca gaactattt tttaaagcct gacaaacttc     3900
ataaatggtg atgtgacttt tcttcttaca tgctgaatca ctggtggaaa cgttaggata    3960
agcaagaatt gccagaaaat aaagtagaca gatctttctc tttgtctgcc ttgaatattg    4020
cttccatgta ttttggaaaa gaaatgatt tcatttataa atgaacatac taaaatagtc     4080
atgtatagcc tctagcattt taaattattt ttattatta gaaagaaaat atattttttc      4140
ttttcattgt caaatatctt ccctatatct aaacaatgca aatctaaat gaataagtgg     4200
```

```
tcagactcct taatgtgttt ttctcttctt tctctcttt tctttgagga gaatgatggt    4260
caccaccaca attaattgta attaagggaa atgaattatt aaaacaattt taaaatggcc    4320
aatgatgtat acatgtattt tagtaaatcc agaaagaag actaagggga caggtgaata    4380
cctgctcctc gcctggatgg gtgtgtattt tgatctgcat tgacaccagc tcttaataaa    4440
tggaaactta tttattttca cagttgaaag tcatattttt gtagttctag ttttcattct    4500
gtagttctca ccccttttgtt catattttta aagggaagac cttctgctgc ttttctacaa    4560
ttggcagatc aggtttgtct ggccaactaa ggacaccagg aggggttgtgg gcacacctgg    4620 gatgtggaag ctgaggacca gatgcacaca aggcattgct ctgtttgctg ttctagtggt    4680
ggagactcct acgtgctgtt atgcttctca ttttatattt ccaaaccacc tgagcgagta    4740
atgtcaactt cgggagggtc tggtggactt tctccccact ccccaagtct cagagctttt    4800
agcctggaag tttgtaaaac tgattagtag ttttacttta ccataggatg tgagagggca    4860
gtcattcttc tcactgagtt tttgtttaaa aaccaggaaa tttctacaat catggagaca    4920
gattttaatt tgcatgctct cctttattta gttgctgggg ccaaacacat gaacttgtta    4980
caacaattta aaataataa taacaaaagg aaagcaacga atgcacttca tatagactgt    5040
tagaaaaggc ctttgaaaat taccagcagt gaaatcaaat aaattagcca ctttaaactg    5100
cggtcaaaag attttttctag ccatcagatg caattacgat gtctcagagc tctgctatcg    5160
cttgcatgct cggtgtacag tctcccggca actgttttgt tccaatcaac ttagcaagtc    5220
tttcaacttt aaaattatca atctttgata tgatcatcaa ggtctctgga aagcatgga    5280 tgtaatagtg atttctatt tcttaaaaaa tgtaaactgt ggacacttaa tggaaccaag    5340
ctaaccaaag tatctccccg aagtttcatg atatctagtc cattaactct ttgggccatg    5400
acctgtggta cctagttatg gtagtgcaaa tcagatcaga gcaaagcaat gagatcatca    5460
tgaagacata tgtccactaa gtactccaat taccagcgta ggcaaaatga gcttccacct    5520
ctgtccactc cctgcagagc caatatagtc gtgcttccac ctcgtaggca ttgtcctgca    5580
gtgatttgtc ggactgtggt tactctgtcg tcacattttg tagaattagt tctataaaag    5640
tattgtgaat acaatgtatg tccaattgga ttgtttaaaa actacttata attaatcact    5700
agcctactca gcagactaaa atgatgtcaa cagtctatat tcaggcttat aaacatttct    5760
tggtttccaa cagaagtcaa atgtgtttgt ggggagaacg ttttgctagg attttgacaa    5820
ctttcctgaa agctaggcct tttttacata atgattttgc attggggtca ccttagtata    5880
ttcacgtcaa tccacgctct tctttccttc gtgaaccata gtgggctctt cactcctgct    5940
cgtaataacc acctccaaat ttgttagagt gatttggtct cctctggcag ctgtggtgg    6000 ccacataaag gatcttccat tagagggaca caggacacaa agctccattc ccatgaccct    6060
ctcttccctg tgtctcccct aacaaggcaa tctggaagca gaaatgcaaa ctccagcccc    6120
accacacatc caccgatgca tttgtggcta gaaatttaa tctaaacttt ttttaaaaaa    6180
aatcataata gttaggatag tttcctatag caaagggctc cttgattcat aagcacctcc    6240
cccccaaaaa aaccaaattg gtaaaaattc atttctttt aaatagagca ataagttcat    6300
actgtgttgc cgttgtaata atgaattgtt ctggactaga aaacaaaatg aggcattttg    6360 ttaaggggt aggaaaatga ctgattgttg ggccctttgg caaagctgg tgcctggtaa    6420 gtagaaacga aatggaaaca gaaataacat ttgtgaaatc actggagggc tcaagcaaat    6480
gccagagctt ctccctggct tgttcctact tgttgagctc tttggccctg agtcccatcc    6540
atctccactg caacagtctg tctttctgcc tacatccgcc tgagaccaag gagggtcttt    6600
```

```
ggtacagtcc acattatgag gctctgattt cctatcccag tttagggctc cagaaaagcc    6660
attctcccaa actaatgatt cttgggtgct gtgggtcacc aacaggctgt ttacaaagca    6720
gaaaatatca tcaccatcat aacctttctc cttgagaaaa cttttatttt tgtctaagca    6780
attttatatt ttagaatatc atcttgaacc attataaaac accttaaata aaagtgattg    6840
tgactaaggc acgttggaga acattccaat cttttcctccc aagggttctg gcaccttatg    6900
atgtactttg taaaaaaatt gattgaagat tttaaataaa caggaaatta gaagtgttag    6960
ggttagataa aggaaaagtg aaaaagcata agaaatttgg gacttttcca tgttgaaagg    7020
agaaaaagca caagttccct agttaccatt taatatgagg gtgcaagagc cacatttaca    7080
aacaacaaac ttgatcttta aaaatgtttt taaaactctc tgagtctcag tgacttcatt    7140
tgtaaatgag agtgattcat ctagatgact ctaaggtctc tttcaggtcc caggggacgt    7200
gatctaagtt aggagtggga acatgggagt ggctgcttct ccttggctaa gcccatgcag    7260
actattgtgt ccaggactgg aataaaggtc ctttttgctg catcacccag gcaacactcc    7320
cagccttact caggagtggt gaacattttc tgctctggac atagaatagg taggttcatt    7380
cctggtcttt tcactttaga ttctctttag gttcaagatg cagatttctc aatttggaca    7440
cacctgcatc acgttggtca aattttgctg cctgtttcta gggttttctt ctcagtttca    7500
tccctgcctt ccctttttg ttgttttttt tttggttcaa ggcccagctt cagttaatcc    7560
cttcatctct atgccatgtc tccaattcct agtatgtaac tagaggttca agagacccca    7620
aattcctgcc attttcccca tttatgtttc cccatgtgaa tcttcaggaa gtaaccagtc    7680
ttccttctca cttcatttcc tgtcctctgt ttatttggtt attttctttc attaataaac    7740
taaccatctc ttagctactt acattcacaa atgtaatttt aatctattgt gtttcattgt    7800
gaaagagaat ctcattgaag gaaggaagga agaaattgag gaataaaggt aggaagggag    7860
agaaacaaag actatccaac caattgactg agatgtgagc cggcttgact cctaggagac    7920
taagtagatc cattcagctt gaacactgag ttccagggca gaatctgtcc attttctgtt    7980
ttgttcttac ttgctgcttt tggaatggtg gtaaagccac cagtcaccat gagccttgaa    8040
aggaccttca ctaatgagga cttgactcac cctcttttaaa aagcaaaaga aacagaattt    8100
acttacaatc ttctggtaaa ttaccttttct gatcctctcc ttattcccaa aaggcaattt    8160
ttttaatcca gcagagatga tttagcatat aaatcccagg tcatttgagg aggtgatgac    8220
gctatttgga tttatttatg agacagtagt aattataaat gattcctagg cagtttgtac    8280
tagtttggtc atattggttg tttaagtgga gtctcttctg attgtttgtt tccaataaag    8340
tatcagttgt taataatttc aagatttcca taaaaataag aaaacttgga aaacattttt    8400
aattttattt cttaagagac cacagagcct aattttcaat ttttatggta agcttgctta    8460
aaacatgtat aaaaagaagc ctacatgctc aaaggcagag gcacctttag ccctacaaca    8520
gttggaagct ccatgatatc acagccccac atggatagat tggagaaaga attctgactt    8580
agaccacctg tagcagacct tcctcttttg gcatattttt ttaatcacaa aaaggacctg    8640
agactcccta tctgaagata agccaaactt ggggtataca ttaagaatct gggaagaaag    8700
aaaaaaaaga aaaagatata ataagcagta ttttaaaata ccatgagtta tgggcatgca    8760
tatggtacaa agagtagttc tttggggttga aagaaagaag agtttgcatt gaactgcgta    8820
ggctggcaag aatgcagagg tatacaatgt ttgatgggct ttggaggcat ttcaatagta    8880
aatgggtgac aggactggaa agatgtgaaa tatgagggtt ttccagggag atgggactta    8940
atgggccatg atgtatttgt aggaatgtga tttcaataga ttgactattt tgtctactgt    9000
```

```
gataagtttg tgtaggggaa ctgaggaaaa ctgagatgag acttcatgga aggggctaca      9060
aagtacagtc taaaggccta gataaagttt gaaacttgat ttagaaagtc atgaaaagcc      9120
actcagagtt ttaagcaaag agtgatgggg cagcaatggc tgtgcatttt tcaggttgaa      9180
agtagtgaga tgtcagttct tcctggaaga tatcatgaga atgcacacaa aactgaacat      9240
tttctcagca gcaaggagtg ctaaaggtg cacactccaa gtcaacaact caccgtgtgc       9300
agcaccttcc tcacacattt tgctttgctt tctgtcacag gaccatcaga cgtagaacgt      9360
cctgactctc ctgaattact agaatgtcag caacaaactc acaaagtaga ttagagggta     9420
ggaatagata cataaatttt taaaaacctg ccaatcatac tgttttctag acagtaatat     9480
aataagaaca tgaggcagga catccacaaa tagtagagaa taattaatag tccagaactg     9540
ccaaatagga attcccctta tgaaaacacc cttgcagcta atcaggtagc ccttgtttag     9600
aaaccaatta gcactcataa aatatttgta caaggagtga gtgggggaga atgagcaca      9660 atatgggttc tgccatcaat cagcttataa tacaactaaa gaaagaaaac atgctcaaag    9720
caccattaga gaaagggtga gccctaatga catagtttca cattcaatat ggtaggagtt    9780
gaaacaaggg agaaatgctg tggttttgaag tggttcaaca aggtaggatt tctagagaaa   9840 gggggggttta ggagttagat aagtagagga tcagcattct aggtatgaag gcaggattat   9900
ctggcatgtg gcagggtgaa tgatgttaat cagtaactgc taattgatat ttactgagca    9960
gctgctgtgt cctcacgatg gtaagactat tagaggaaga cagcccacct gcctaactgg   10020
gaacacaagg cacacatata ttggaaagat catgttgcac aaaacaggtg ttcaataaat   10080 aattttttgaa taaatgtgaa cactgaatag caaataaatg ttatagatcg taatagttgt  10140
agaagattgg ttgggattgt agggactgga tgtgggcaa tggctgtggg tctagagtat    10200
attcattgtg cagtggacac acacctaatc tgtcctcaag gacagaacca tgtggaggaa   10260
taggaaaaca agagaagcag gcaagaagcg gaggcagtga gtacagcagc taagaaatgt  10320
tacattgggt tcatccagag caagaaaagc tgagagctgt ccgtgaggga aggccacaca   10380
ggcaagagga gtgggacagg ggagtaaagg agtgggctac aacaggccct gcagatgtgg   10440
aagccagacc cacagaggca cttagaaagt gaggatcctg gatgaattat tttagggaga   10500
aagtgtaggt ttagatcagc tggcagatgt gtttgtgggc tacagccaag ttttcagga    10560 ctaagaagga gcaaaataag tagaacttct tgggacagga gatctagggt actccagaac  10620
cagggaaatg agaaacaaga ggggaatttt aagaaagaga gggaagatca tctatgaggt   10680
tggagatgaa aggtgttgga gatggtgagg cacaagtcaa aagactcact cgaagggcag  10740
gaactctgct tatttgtcca tattcccaga gtttgtcatg aggtctggcc cacgtgggca  10800
gtcactcggc cactatgtat cactgtggct gccatggtgg atgaggctg acagaacct    10860 gtggtgatcg gcagtctttc tggaggactc accagggagg ggtctcaggg tgggcatctc  10920
ctttcacctt cctgtgcatg tcactgcact gttcttcttc cctccctgaa cagcacacac  10980
actgcatcct tagtttcagg ggtctgaaaa caaatgctac gaccaccttg ctttggtggc   11040
ttttctgaac aggcattgtg agaagagatg ttctggccag gtgaaagtgg actttatttt   11100
taggtaggtt tttcagttta gaaaggtttc ctttgcttat cccttgagga cttctgtgct   11160
gctgcttctc ctccatcttg ctagttaaca gaacaggggc agaagtgaca ccaatgctct   11220
cggccatgcc tgccttggga agcactaccg ggccccactg tttagaatct tagatggaaa   11280
tgtacacaag gcattgacac acgcctgcgg gagtgaccca gtgcttccct cccatgggac   11340
tcagggtcag cgtgggaagg cagctggcag ggacaggagc cccgcccgca aggtggactg   11400
```

| agcctcactt | ccacacaaaa | ccagagtccc | atctgcccca | gagcgctcgc | tctcctcccc | 11460 |
| ttccttccgc | tcaatgcagc | ctgacacgcc | tttgaccaga | actgcaacat | ttcaaacaca | 11520 |
| aacccagatc | tgttgggaaa | tcctaattaa | aaacgttgca | ttcccaggtg | gcacaatcac | 11580 |
| atcctgccta | aaacttctgg | cccacatccc | accacccaga | tgttgaaaag | aaacctttct | 11640 |
| ctgcttaaca | ccaaaacctg | cacttcaagg | tttctttagg | ggacaaagaa | aaaaaagta | 11700 |
| cacacatgca | gagttcagcc | tacatgttca | ttgaggaaaa | agagcgtggc | ttattcatct | 11760 |
| ttcaatcttt | tgattgttgg | cattatgatt | atgattatga | ttaattactc | tgacctgaca | 11820 |
| ggaattgaag | aagagactat | atgctggtgc | tctgaaatga | tctacccaac | tctgtcatct | 11880 |
| gtaacaacca | gtgataactc | tcttgtcttg | taaaaagggt | ttgtacataa | cttgtacatg | 11940 |
| gtttcatttt | gtattttccg | cagattaaaa | atttatgtat | ttgtgttcta | aaa | 11993 |

<210> SEQ ID NO 8
<211> LENGTH: 6103
<212> TYPE: DNA
<213> ORGANISM: Homo sapiens

<400> SEQUENCE: 8

| cgccaggtcg | cgcacagcgc | cccgagccca | ggcgcctccc | cgccccctc | ccgcgctccg | 60 |
| cggcggcggc | ggcggcggca | gcagtagcag | caatatggct | gttgatgggt | gtttggggtg | 120 |
| gcgctggcgg | cgggaggagc | tcccccgagc | ccctgcgccg | gctgcccgtt | gctagctatg | 180 |
| gcaaatggtg | gcggcggcgg | cggcggcagc | agcggcggcg | gcggcggcgg | cggaggcagc | 240 |
| agtcttagaa | tgagtagcaa | tatccacgcg | aaccatctca | gcctagacgc | gtcctcctcc | 300 |
| tcctcctcct | cctcttcctc | ttcttcttct | tcctcctcct | cttcctcctc | gtcctcggtc | 360 |
| cacgagccca | agatggatgc | gctcatcatc | ccggtgacca | tggaggtgcc | gtgcgacagc | 420 |
| cggggccaac | gcatgtggtg | ggcttttcctg | gcctcctcca | tggtgacttt | cttcgggggc | 480 |
| ctcttcatca | tcttgctctg | gcggacgctc | aagtacctgt | ggaccgtgtg | ctgccactgc | 540 |
| gggggcaaga | cgaaggaggc | ccagaagatt | aacaatggct | caagccaggc | ggatggcact | 600 |
| ctcaaaccag | tggatgaaaa | agaggaggca | gtggccgccg | aggtcggctg | gatgacctcc | 660 |
| gtgaaggact | gggcgggggt | gatgatatcc | gcccagacac | tgactggcag | agtcctggtt | 720 |
| gtcttagtct | ttgctctcag | catcggtgca | cttgtaatat | acttcataga | ttcatcaaac | 780 |
| ccaatagaat | cctgccagaa | tttctacaaa | gatttcacat | tacagatcga | catggctttc | 840 |
| aacgtgttct | tccttctcta | cttcggcttg | cggtttattg | cagccaacga | taaattgtgg | 900 |
| ttctggctgg | aagtgaactc | tgtagtggat | tcttcacgg | tgccccccgt | gtttgtgtct | 960 |
| gtgtacttaa | acagaagttg | gcttggtttg | agattttaa | gagctctgag | actgatacag | 1020 |
| ttttcagaaa | ttttgcagtt | tctgaatatt | cttaaaacaa | gtaattccat | caagctggtg | 1080 |
| aatctgctct | ccatatttat | cagcacgtgg | ctgactgcag | ccgggttcat | ccatttggtg | 1140 |
| gagaattcag | gggacccatg | ggaaaatttc | caaacaacc | aggctctcac | ctactgggaa | 1200 |
| tgtgtctatt | tactcatggt | cacaatgtcc | accgttggtt | atgggggatgt | ttatgcaaaa | 1260 |
| accacacttg | ggcgcctctt | catggtcttc | ttcatcctcg | ggggactggc | catgtttgcc | 1320 |
| agctacgtcc | ctgaaatcat | agagttaata | ggaaaccgca | agaaatacgg | gggctccctat | 1380 |
| agtgcggtta | gtggaagaaa | gcacattgtg | gtctgcggac | acatcactct | ggagagtgtt | 1440 |
| tccaacttcc | tgaaggactt | tctgcacaag | gaccggatg | acgtcaatgt | ggagatcgtt | 1500 |
| tttcttcaca | acatctcccc | caacctggag | cttgaagctc | tgttcaaacg | acatttact | 1560 |

```
caggtggaat tttatcaggg ttccgtcctc aatccacatg atcttgcaag agtcaagata   1620
gagtcagcag atgcatgcct gatccttgcc aacaagtact gcgctgaccc ggatgcggag   1680
gatgcctcga atatcatgag agtaatctcc ataaagaact accatccgaa gataagaatc   1740
atcactcaaa tgctgcagta tcacaacaag gcccatctgc taaacatccc gagctggaat   1800
tggaaagaag gtgatgacgc aatctgcctc gcagagttga agttgggctt catagcccag   1860
agctgcctgg ctcaaggcct ctccaccatg cttgccaacc tcttctccat gaggtcattc   1920
ataaagattg aggaagacac atggcagaaa tactacttgg aaggagtctc aaatgaaatg   1980
tacacagaat atctctccag tgccttcgtg ggtctgtcct ccctactgtt tgtgagctg   2040 tgttttgtga agctcaagct cctaatgata gccattgagt acaagtctgc caaccgagag   2100
agccgtatat taattaatcc tggaaaccat cttaagatcc aagaaggtac tttaggattt   2160
ttcatcgcaa gtgatgccaa agaagttaaa agggcatttt tttactgcaa ggcctgtcat   2220
gatgacatca cagatcccaa aagaataaaa aaatgtggct gcaaacggct tgaagatgag   2280
cagccgtcaa cactatcacc aaaaaaaaag caacggaatg gaggcatgcg gaactcaccc   2340
aacacctcgc ctaagctgat gaggcatgac cccttgttaa ttccrggcaa tgatcagatt   2400
gacaacatgg actccaatgt gaagaagtac gactctactg ggatgtttca ctggtgtgca   2460
cccaaggaga tagagaaagt catcctgact cgaagtgaag ctgccatgac cgtcctgagt   2520
ggccatgtcg tggtctgcat cttttggcgac gtcagctcag ccctgatcgg cctccggaac   2580
ctggtgatgc cgctccgtgc cagcaacttt cattaccatg agctcaagca cattgtgttt   2640
gtgggctcta ttgagtacct caagcgggaa tgggagacgc ttcataactt ccccaaagtg   2700
tccatattgc ctggtacgcc attaagtcgg gctgatttaa gggctgtcaa catcaacctc   2760
tgtgacatgt gcgttatcct gtcagccaat cagaataata ttgatgatac ttcgctgcag   2820
gacaaggaat gcatcttggc gtcactcaac atcaaatcta tgcagtttga tgacagcatc   2880
ggagtcttgc aggctaattc ccaagggttc acacctccag gaatggatag atcctctcca   2940
gataacagcc cagtgcacgg gatgttacgt caaccatcca tcacaactgg ggtcaacatc   3000
cccatcatca ctgaactagt gaacgatact aatgttcagt ttttggacca agacgatgat   3060
gatgaccctg atacagaact gtacctcacg cagccctttg cctgtgggac agcatttgcc   3120
gtcagtgtcc tggactcact catgagcgcg acgtacttca atgacaatat cctcaccctg   3180
atacggaccc tggtgaccgg aggagccacg ccggagctgg aggctctgat tgctgaggaa   3240
aacgccctta gaggtggcta cagcaccccg cagacactgg ccaatagcga ccgctgccgc   3300
gtggcccagt tagctctgct cgatgggcca tttgcggact taggggatgg tggttgttat   3360
ggtgatctgt tctgcaaagc tctgaaaaca tataatatgc tttgttttgg aatttaccgg   3420
ctgagagatg ctcacctcag caccccccagt cagtgcacaa agaggtatgt catcaccaac   3480 ccgcccctatg agtttgagct cgtgccgacg gacctgatct tctgcttaat gcagtttgac   3540
cacaatgccg gccagtcccg ggccagcctg tcccattcct cccactcgtc gcagtcctcc   3600
agcaagaaga gctcctctgt tcactccatc ccatccacag caaaccgaca gaaccggccc   3660
aagtccaggg agtcccggga caaacagaag tacgtgcagg aagagcggct ttgatatgtg   3720
tatccaccgc cactgtgtga aactgtatct gccactcatt tccccagttg gtgtttccaa   3780
caaagtaact ttccctgttt tcccctgtag tccccccctt ttttttttaca catatttgca   3840 tatgtatgat agtgtgcatg tggttgtcat ttttatttca ccaccataaa acccttgagc   3900
acaacagcaa ataagcagac ggaccaaaag ttatttatga ttctggggga aaaataaccc   3960
```

| | |
|---|---|
| aaaggcatgc tccagacata aatagctcac tgcaggaacg agttcacaga ttagaaggga | 4020 |
| gcacttgtga tcaacgtcag ttaggcagag caagtttatt taatgtaaaa gaaaagttga | 4080 |
| ttctgattta tcaggattat cagggtgctt tgggttttga ttttgttgtt gttgttgttt | 4140 |
| tcctttcttt cttttttttat acacacaata agttagcaca tgtttatttg aaacaagcaa | 4200 |
| ccaaacagca atgaaaacat attgattgtt tccagtctct gggccgaagt attgcgaagc | 4260 |
| atttgaaaag ctttcacgat ttgtgtagat gattatgaag gacctgcttg ttgcaagaga | 4320 |
| acatcagtga ttttttttagt tactcaccaa ggccttttgt cccagagcca gttccctctg | 4380 |
| ggagttctta tgaacatttc tcaccttaat atggaggaga gaatagtatt ccaatcatgg | 4440 |
| atgtatcaaa ttctagtcat ttagtttaag tgaaagagg tttgattgca tattaaattg | 4500 |
| ttattctgtc tccttatgtt gccatatgaa tagctatttt ttttctttca cttttgacat | 4560 |
| ttgggatgaa aagccatatg tatcataaat atcagatgta agtcattaaa aactgccttc | 4620 |
| ctgggacttt tacatctttt aaaggtgaa ttacttacct tatgtacaga ataaataatg | 4680 |
| ctcaggaaag agcaagtatt tttccatgca ttctcagggg atcttttttac tccccttttgt | 4740 |
| ttgattagtt agggccccaa tgccaggtag gaggaagggc tggggcaatg gtagagtgag | 4800 |
| aggaagacaa acccagctgc agatcatgct tttctaggag ccgacatgct aaataaatta | 4860 |
| gaatgtagga ggatcagcca cagttgactc aacaaagaca aaagccagcc accaccttca | 4920 |
| actgttggca cagctgtgcg gtgctggctg tcccaatgca gaaagctggt gggaaggaat | 4980 |
| tcctcatcat cactttcttt aatgtagcca atttaggcag ggtaatgacg gcaatagaga | 5040 |
| gctgctcctt gtcattatga gacgtgggat aagaagagtg caacagtgag ccaaacacat | 5100 |
| tttggtatag ttattttttt cttcttttgt ttttctttctt ttttaacact tagtaagcat | 5160 |
| gagaggagag gtagaaaaat acccttttt caacatatag ttgtcagatg ctttgtgcat | 5220 |
| gcaaatcatg ctttaggcag tgcggtattt cttaaaaact ggccaattca ccataaccaa | 5280 |
| tttcccttat ggatggacta ggctggtata tacatatttg aaaagttta cttcaaagaa | 5340 |
| ttccatcgaa tagaataggg gtaaaaggga ggaggaaaac atgtcacagc tgtaccatct | 5400 |
| ctaaaaaggt gtttttatgg tgaatgtttt ggatttagat tttggatccc ccgtcccctc | 5460 |
| aagcatgata gttttggata tttgcttgct gtgtgaattg acaagcactt ttactgacaa | 5520 |
| atggtgaggc tcagtcagaa cctccacccct cccccacacc aaagacaggg gcagcgtagt | 5580 |
| attcaaaacca gtattgtggt ggggaataat tgtatacatg taaattatca agccctatga | 5640 |
| gtggaagaat ttttttcaaat tatttttgtc cctctatata ttgatttata ttatgtataa | 5700 |
| ctatctcttt atataaacta tatataatta tatatatata actatataat tatatatata | 5760 |
| taactatata tataactata tatatgtatc ccctagtatt ggatcatgaa gagctcttca | 5820 |
| tgcattctttt gcaaaggagg ttataaagtt acgccctcag aacatttata actataagaa | 5880 |
| tgtgccagtt aaagtgctca acaggaaata tgacagttta aaagcattgt aaaactcaca | 5940 |
| tagcttactt ctctctctaa agtgcaacaa ggatgaatag aatgggccaa ggtatgacaa | 6000 |
| ttaatggttc tgcatgacct agccactgct ggggtttttc ttctataacg ttgtccttgt | 6060 |
| gaaaactttt gtgaaattaa aaaaaaagga gttacaaatt tta | 6103 |

```
<210> SEQ ID NO 9
<211> LENGTH: 4494
<212> TYPE: DNA
<213> ORGANISM: Homo sapiens
<220> FEATURE:
<221> NAME/KEY: misc_feature
<222> LOCATION: (2161)..(2260)
```

```
<223> OTHER INFORMATION: n is a, c, g, or t
<220> FEATURE:
<221> NAME/KEY: misc_feature
<222> LOCATION: (2573)..(2672)
<223> OTHER INFORMATION: n is a, c, g, or t

<400> SEQUENCE: 9
ggatcccctt cgtcccacct ggtccacccc agatgctgag gatgggggag ctcaggcggg      60
gcctctgctt tggggatggg aatgtgtttt tctcccaaac ttgtttttat agctctgctt     120
gaagggctgg gagatgaggt gggtctggat cttttctcag agcgtctcca tgctattgtt     180
gcatttccgt tttctatgaa tgaatttgca ttcaataaac aaccagactc agttcttggg     240
gcccttgttt gcactccctc tgggtggagc tgttggatga gggaggggaa gcggagtctt     300
ccatttcccc attcttcaag ccatgggcct actgggaact gcaattcctt gattctcccg     360
gttttttcctg tcctccagca acagcattaa ttcagttaac atttaccggg ggcaactgtg     420
ctggacagag gccagttcct ggaaaagctt ttcccacgcc atcccactgc agacatccct     480
ccttacctcc ccaggaacag cagtctctgc ccacctgacc ccgcccacca gactgaggct     540
cacttcacct ctgacctgag cggccccccag ctcaccaggc cacaggccca agcagtgctc     600
cctgatgcgg cgtttataat ccgctcagcg tgcaggccga ggcaggaggg tgatgaaagc     660
tgggcaggct ccaagaggag ggagttttga tatgtccctg aaagattcat ttagacttca     720
gtcggctaaa ggaggacatg atttggggc caaggaatct gttgaattca gaacacaacc      780
agaggtctgc agggtcaggg atggaggagt gggctttccc atcgccaggg cccactcctc     840
ttcctgctttt tcctgcaggc gccactggga ggtgctatgg ctgtgcctcc cctgggctct     900
ggagcatgtc cagttgcagt gggcagaact gcggaggcgg gccctcctc tgccaggcct      960
ggcagccccc tcctagggcc ttgtttggct agggggtggtg ccgggtgtgg cagtgtgtgt    1020
gtagtggaga gtgttaggtc ttccctacca ggtgcccttg caggggagtg ccacagcagt    1080
cagtccaggg atcccaccgt tagtctcacc ttttttaacc tcttatctct ccccaagatc    1140
cctgaagcca ggtacgagca agatgagagt gggttatctc tggagtgaca gaggctggtc    1200
tgttttccag gctggtaggg actgttccta aagggaggaa gggatgatac cagcctcctg    1260
agcctccttc tcctgcgtta gtgtctcagg ccctgccagg ccttatagac cctcttattg    1320
acactgccca ctggatgggg accggagttg gactcagctt ctgccgaacc ctcaaatccc    1380
agccccaact aaagcatata actcaagacc tacctgcact gaaagctctt ctcaacctga    1440
gcagggtggt ccaattgaaa gggtgggtgt gaccacctct cctgcaccca tgcgggttgg    1500
cagaggtgtg caggatctgc cacttaccat tcaccatgtg gccttgagga agacgcactc    1560
ggggcctcag tttcctcatc tataaaatgg ggatgtaatt acaccctcac actgtagctg    1620
tgagtattca atgagagcac tgcaaagggc ctggtgtgga gtaggtcctc aggaaaggtt    1680
ggatcccatg tccatcaga gctaaaagcc ccaggaggag agggtggctg gtttgtcccc    1740
acaaacccct gggattcccg gctccccagc cccttgcccc tctctccagc cagactctat    1800
tgaactcccc ctcttctcaa actcggggcc agagaacagt gaagtaggag cagccgtaag    1860
tccgggcagg gtcctgtcca taaaaggctt ttcccgggcc ggctccccgc cggcagcgtg    1920
ccccgccccg gcccgctcca tctccaaagc atgcagagaa tgtctcggca gccccggtag    1980
actgctccaa cttggtgtct ttccccaaat atggagcctg tgtggagtca ctgggggagc    2040
cgggggtggg gagcggagcc ggcttcctct agcaggagg gggccgagga gcgagccagt    2100
gggggaggct gacatcacca cggcggcagc cctttaaacc cctcacccag ccagcgcccc    2160
```

```
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn atcctgtctg tccgaaccca   2280
gacacaagtc ttcactcctt cctgcgagcc ctgaggaagc cttgtgagtg cattggctgg   2340
ggcttggagg gaagttgggc tggagctgga caggagcagt gggtgcattt cagcaggctc   2400
tcctgagggt cccaggcgcc agctccagct ccctggctag ggaaacccac cctctcagtc   2460
agcatggggc cccaagctcc aagcagggtg ggctggatca ctaacgtcct ggatctctct   2520
caaactgggc aaccccgggc tcattgaaat gccccggaat gacttggcta atnnnnnnnn   2580
nnnnnnnnnn nnnnnnnnnn nnnnnnnnnn nnnnnnnnnn nnnnnnnnnn nnnnnnnnnn   2640
nnnnnnnnnn nnnnnnnnnn nnnnnnnnnn nnccggggtga aagcagagtg ctccctgacc   2700
ctctgcccct ccctcctcca ccctggcctg ctttagcttt ccccagacat ggccaacaag   2760
ggtccttcct atggcatgag ccgcgaagtg cagtccaaaa tcgagaagaa gtatgacgag   2820
gagctggagg agcggctggt ggagtggatc atagtgcagt gtggccctga tgtgggccgc   2880
ccagaccgtg ggcgcttggg cttccaggtc tggctgaaga atggcgtggt gagtggcacc   2940
ctgggctagg gcgctggggg gctggggtgt gaccccctgt gagtcctggg ccaatccctg   3000
aggactgcta agctgcgtcc tatgccctat gcctggtaga ttctgagcaa gctggtgaac   3060
agcctgtacc ctgatggctc caagccgtg aaggtgcccg agaacccacc ctccatggtc   3120
ttcaagcaga tggagcaggt ggctcagttc ctgaaggcgg ctgaggacta tggggtcatc   3180
aagactgaca tgttccagac tgttgacctc tttgaaggta gagaggagaa tgctggggga   3240
ggaggtgggc aggaggacag ggtgctggga cagggagagg gtatgaccaa atatgccaca   3300
actaggggtg tgctcgcccg cacacagcag ggatgggata tgccgagaat aacacgccac   3360
gctcacaggg cccactgaga ggcctccctt gaattgggga caactcttgg ccctggtttg   3420 gccattttt tgtgagagac gggggcaggc cctggcttgg agtcttgttt atacgttctt   3480
gatgttcatc tcctctctcc tgtcttctca caggcaaaga catggcagca gtgcagagga   3540
ccctgatggc tttgggcagc ttggcagtga ccaagaatga tgggcactac cgtggagatc   3600
ccaactggtt tatgaagtat gtggccccca gggagcttga gtctccgcat ggggtgggag   3660
gtggcttgtt ctaaggagct tgcgggaagg attaggggaa gcagatagcc aagaaaggat   3720
aaagtgaggg tctgggatgg ggaataatgg gtccttaata ctccttgacc cctcccttttc   3780 cacccctcctg cgctcagtct ccctagccta tgaggcaagc tagattaggg aaaaaaagtg   3840
caacaggaag gcaatgggat tgggctagga cgtaacagag ggatcagaaa acgggtggaa   3900
aacacacagt tctaccaagt ctttatcctg cttcctcctc ttctaggaaa gcgcaggagc   3960
ataagaggga attcacagag agccagctgc aggagggaaa gcatgtcatt ggccttcaga   4020
tgggcagcaa cagaggggcc tcccaggccg gcatgacagg ctacggacga cctcggcaga   4080
tcatcagtta gagcggagag ggctagccct gagcccggcc ctcccccagc tccttggctg   4140
cagccatccc gcttagcctg cctcacccac accgtgtgg taccttcagc cctggccaag   4200
ctttgaggct ctgtcactga gcaatggtaa ctgcacctgg gcagctcctc cctgtgcccc   4260
cagcctcagc ccaacttctt acccgaaagc atcactgcct tggcccctcc ctcccggctg   4320
cccccatcac ctctactgtc tcctcccctgg gctaagcagg ggagaagcgg gctgggggta   4380
gcctggatgt gggccaagtc cactgtcctc cttggcggca aaagcccatt gaagaagaac   4440
cagcccagcc tgccccctat cttgtcctgg aatattttttg gggttggaac tctc          4494

<210> SEQ ID NO 10
```

```
<211> LENGTH: 24
<212> TYPE: DNA
<213> ORGANISM: Mus musculus

<400> SEQUENCE: 10
ttcggcttgg gtcgactctt agaa                                          24

<210> SEQ ID NO 11
<211> LENGTH: 24
<212> TYPE: DNA
<213> ORGANISM: Mus musculus

<400> SEQUENCE: 11
tatgatgagc gcatccatct tggg                                          24
```